United States Patent
Chang et al.

(10) Patent No.: US 9,675,519 B2
(45) Date of Patent: Jun. 13, 2017

(54) SYSTEM AND METHOD FOR PERSONALIZED INJECTION TREATMENT

(75) Inventors: Sobin Chang, New York, NY (US); Kwonsoo Chun, Houston, TX (US)

(73) Assignee: Aquavit Pharmaceuticals, Inc., New York, NY (US)

( * ) Notice: Subject to any disclaimer, the term of this patent is extended or adjusted under 35 U.S.C. 154(b) by 397 days.

(21) Appl. No.: 13/982,213

(22) PCT Filed: Jan. 27, 2012

(86) PCT No.: PCT/US2012/022902
§ 371 (c)(1),
(2), (4) Date: Aug. 15, 2013

(87) PCT Pub. No.: WO2012/109032
PCT Pub. Date: Aug. 16, 2012

(65) Prior Publication Data
US 2015/0034208 A1 Feb. 5, 2015

Related U.S. Application Data

(60) Provisional application No. 61/437,152, filed on Jan. 28, 2011.

(51) Int. Cl.
*A61J 1/20* (2006.01)
*B01F 13/10* (2006.01)
(Continued)

(52) U.S. Cl.
CPC .............. *A61J 1/20* (2013.01); *A61M 5/1782* (2013.01); *B01F 13/1055* (2013.01);
(Continued)

(58) Field of Classification Search
CPC .... A61J 1/10; A61J 1/1418; A61J 1/20; A61J 1/201; A61J 1/2096; A61J 2200/10;
(Continued)

(56) References Cited

U.S. PATENT DOCUMENTS 4,467,844 A * 8/1984 Di Gianfilippo et al. ........ 141/1
4,513,796 A * 4/1985 Miller et al. .................... 141/83
(Continued)

FOREIGN PATENT DOCUMENTS

WO WO-2012-109032 8/2012
WO WO-2015-020982 2/2015
WO WO-2015-020982 A3 4/2015

OTHER PUBLICATIONS

PCT/US2012/022902 International Search Report dated Apr. 24, 2012.
(Continued)

*Primary Examiner* — Timothy L Maust
*Assistant Examiner* — Andrew Schmid
(74) *Attorney, Agent, or Firm* — DLA Piper LLP (US)

(57) ABSTRACT

An automated system (100) for compounding pharmaceutical agents for injection treatment of a patient includes a housing (110) enclosing an interior space; an inventory structure (130) having a plurality of chambers (131) for individually holding one or more pharmaceutical agent— containing single use capsules (102), wherein each capsule has a volume capacity of from about 0.1 to about 10.0 mL liquid; means (140) for selecting capsules in accordance with predetermined pharmaceutical agents contained in said capsules; means (150) for moving the selected capsules to a processing area; means (165,166) for sequentially transferring a controlled quantity of the predetermined pharmaceutical agent with direct fluid communication from each selected capsule to a product container under positive or negative pressure; and means (151) for automatically discarding spent capsules from which the pharmaceutical agents have been removed after a single use.

27 Claims, 29 Drawing Sheets

(51) Int. Cl.
*B05B 15/02* (2006.01)
*A61M 5/178* (2006.01)
*B65B 3/00* (2006.01)
*A61J 3/00* (2006.01)

(52) U.S. Cl.
CPC ...... *B01F 13/1058* (2013.01); *B01F 13/1063* (2013.01); *B01F 13/1069* (2013.01); *B05B 15/025* (2013.01); *B65B 3/003* (2013.01); *A61J 1/2006* (2015.05); *A61J 3/002* (2013.01); *A61J 2200/70* (2013.01); *A61J 2205/20* (2013.01); *B01F 2215/0032* (2013.01)

(58) Field of Classification Search
CPC .... A61J 3/002; A61M 5/3286; A61M 5/3291; B01F 13/1072; B01F 13/1055; B01F 13/1058; B01F 13/1063; B01F 13/1069
USPC .... 141/2, 21, 25, 26, 27, 39, 230, 231, 323, 141/329, 330
See application file for complete search history.

(56) References Cited

U.S. PATENT DOCUMENTS

| | | | |
|---|---|---|---|
| 4,587,793 A * | 5/1986 | Brennan et al. | 53/425 |
| 4,653,010 A * | 3/1987 | Figler et al. | 702/19 |
| 4,712,460 A * | 12/1987 | Allen et al. | 83/208 |
| 4,789,014 A * | 12/1988 | DiGianfilippo et al. | 141/83 |
| 4,922,975 A * | 5/1990 | Polaschegg | 141/104 |
| 5,040,699 A * | 8/1991 | Gangemi | 222/1 |
| 5,085,256 A * | 2/1992 | Kircher et al. | 141/83 |
| 5,431,202 A * | 7/1995 | Dikeman et al. | 141/105 |
| 5,514,150 A | 5/1996 | Rostoker | |
| 5,697,407 A * | 12/1997 | Lasonde | 141/104 |
| 5,935,096 A | 8/1999 | Barrett | |
| 6,048,086 A * | 4/2000 | Valerino, Sr. | 706/10 |
| 6,182,712 B1 * | 2/2001 | Stout et al. | 141/18 |
| 6,951,228 B2 * | 10/2005 | Steigerwalt et al. | 141/105 |
| 6,975,924 B2 | 12/2005 | Kircher et al. | |
| 6,991,002 B2 * | 1/2006 | Osborne et al. | 141/27 |
| 7,171,992 B2 * | 2/2007 | DiGianfilippo et al. | 141/99 |
| 7,194,336 B2 | 3/2007 | DiGianfilippo et al. | |
| 7,610,115 B2 | 10/2009 | Rob et al. | |
| 7,950,423 B2 * | 5/2011 | Poole et al. | 141/67 |
| 8,069,886 B1 * | 12/2011 | Yanke et al. | 141/252 |
| 2002/0035412 A1 * | 3/2002 | Kircher et al. | 700/239 |
| 2005/0283125 A1 | 12/2005 | Barkhahn et al. | |
| 2006/0136095 A1 * | 6/2006 | Rob et al. | 700/245 |
| 2006/0138095 A1 * | 6/2006 | Stellwag et al. | 219/108 |
| 2006/0259195 A1 * | 11/2006 | Eliuk et al. | 700/245 |
| 2008/0059228 A1 * | 3/2008 | Bossi et al. | 705/2 |
| 2008/0140046 A1 * | 6/2008 | Buck et al. | 604/407 |
| 2008/0161782 A1 * | 7/2008 | Chan et al. | 606/9 |
| 2008/0169043 A1 * | 7/2008 | Osborne et al. | 141/1 |
| 2008/0189043 A1 * | 8/2008 | Anno et al. | 702/14 |
| 2009/0281657 A1 * | 11/2009 | Gak et al. | 700/242 |
| 2009/0318833 A1 | 12/2009 | Lim | |
| 2010/0100237 A1 * | 4/2010 | Ratnakar | 700/232 |
| 2010/0196445 A1 * | 8/2010 | David et al. | 424/443 |
| 2010/0241270 A1 * | 9/2010 | Eliuk et al. | 700/216 |
| 2012/0296280 A1 | 11/2012 | Eum | |
| 2014/0014226 A1 * | 1/2014 | Green et al. | 141/18 |
| 2014/0278510 A1 * | 9/2014 | Mclean et al. | 705/2 |
| 2015/0034208 A1 * | 2/2015 | Chang et al. | 141/2 |
| 2015/0216763 A1 * | 8/2015 | Fearnot | 435/374 |

OTHER PUBLICATIONS

EP12703657.2 OA mailed Jan. 29, 2015.
PCT/US2014/049652 International Search Report and Written Opinion dated Feb. 10, 2015.

* cited by examiner

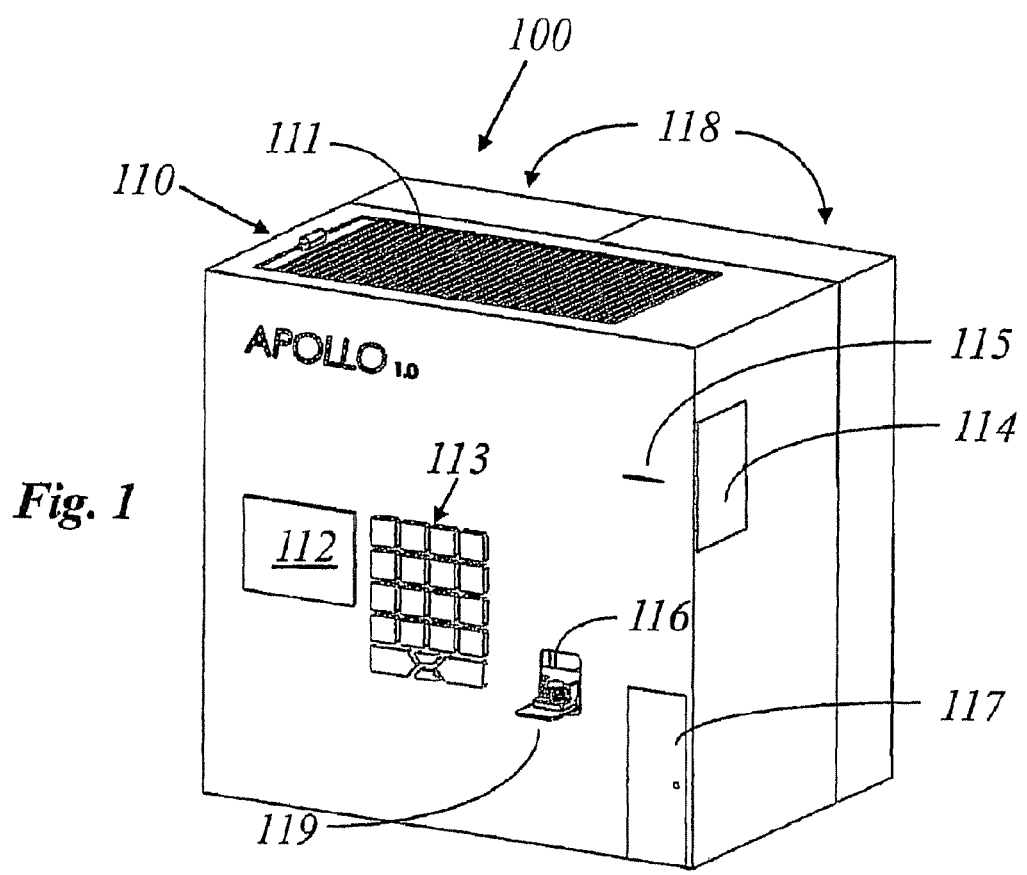
*Fig. 1*
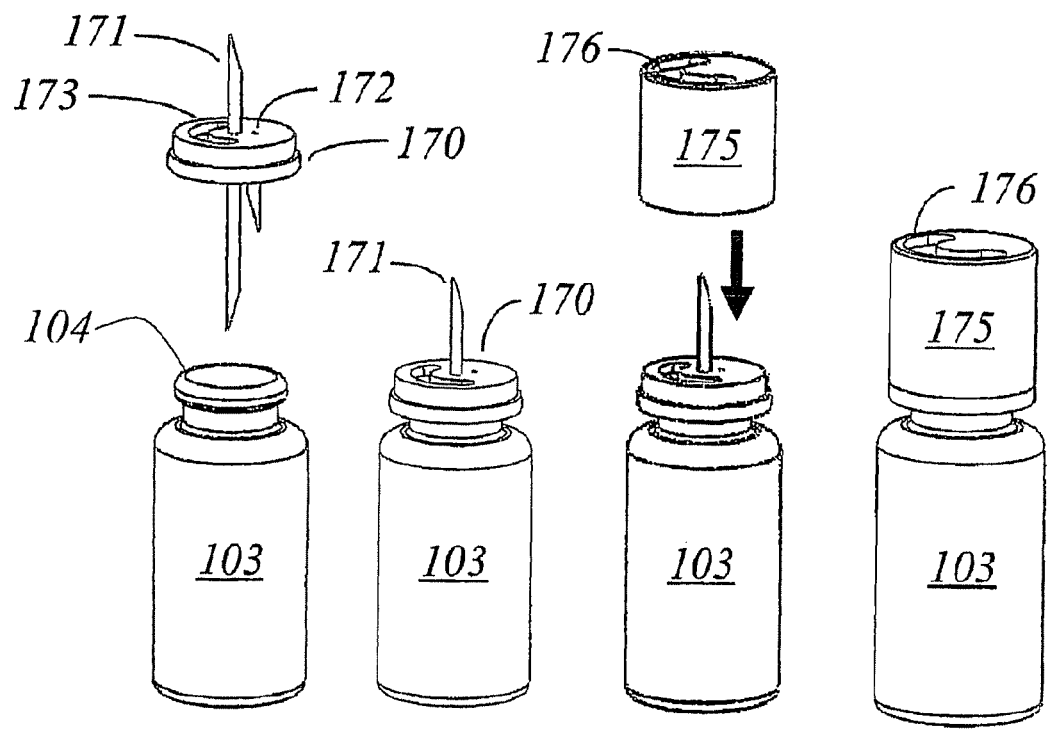
*Fig. 2A*  *Fig. 2B*  *Fig. 2C*  *Fig. 2D*

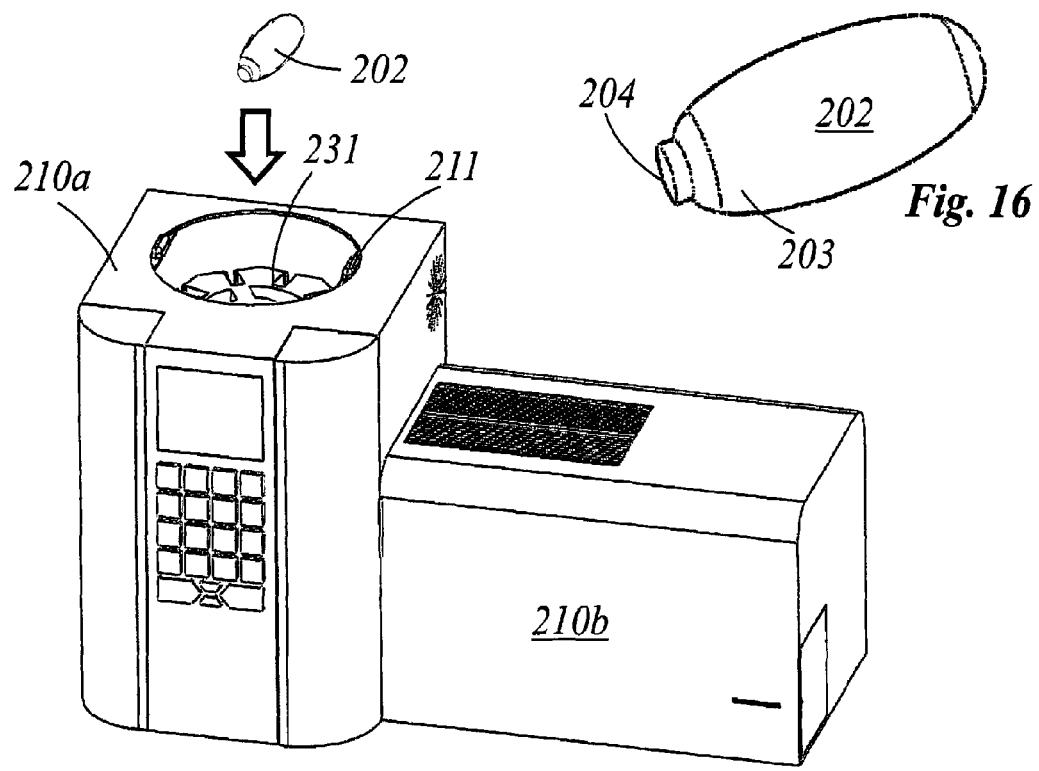
Fig. 16
Fig. 17
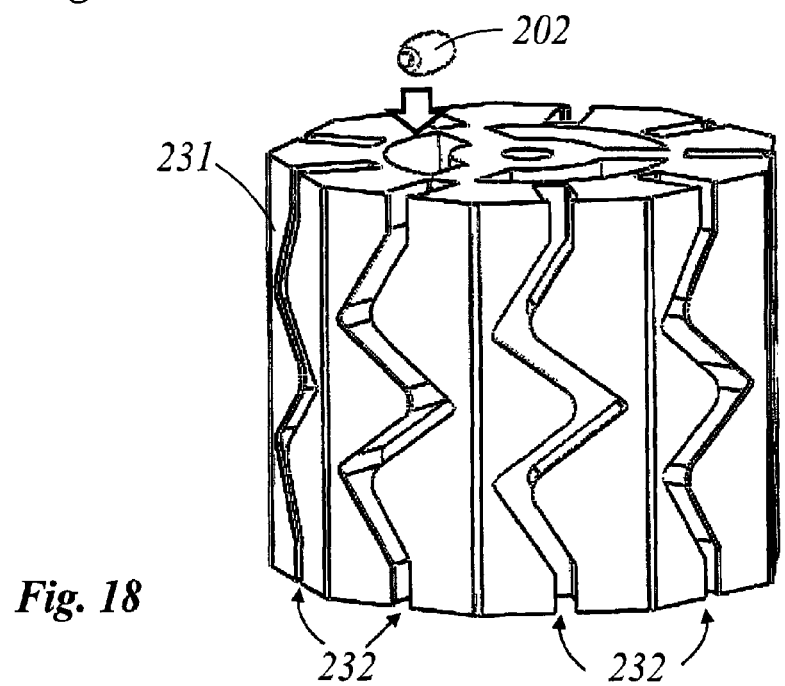
Fig. 18

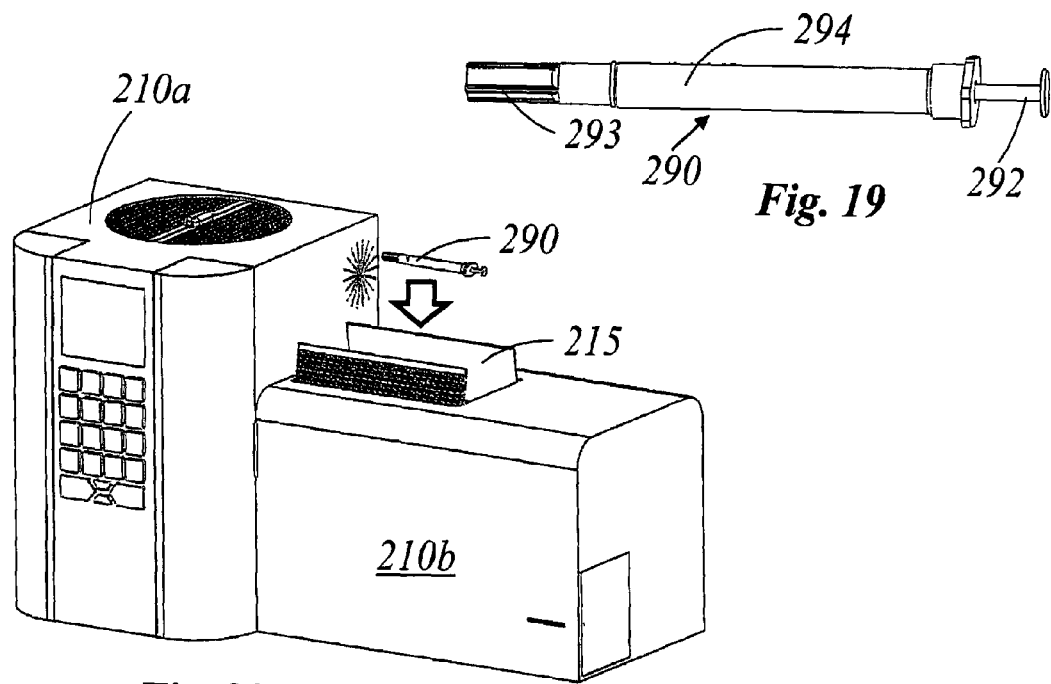
Fig. 19
Fig. 20
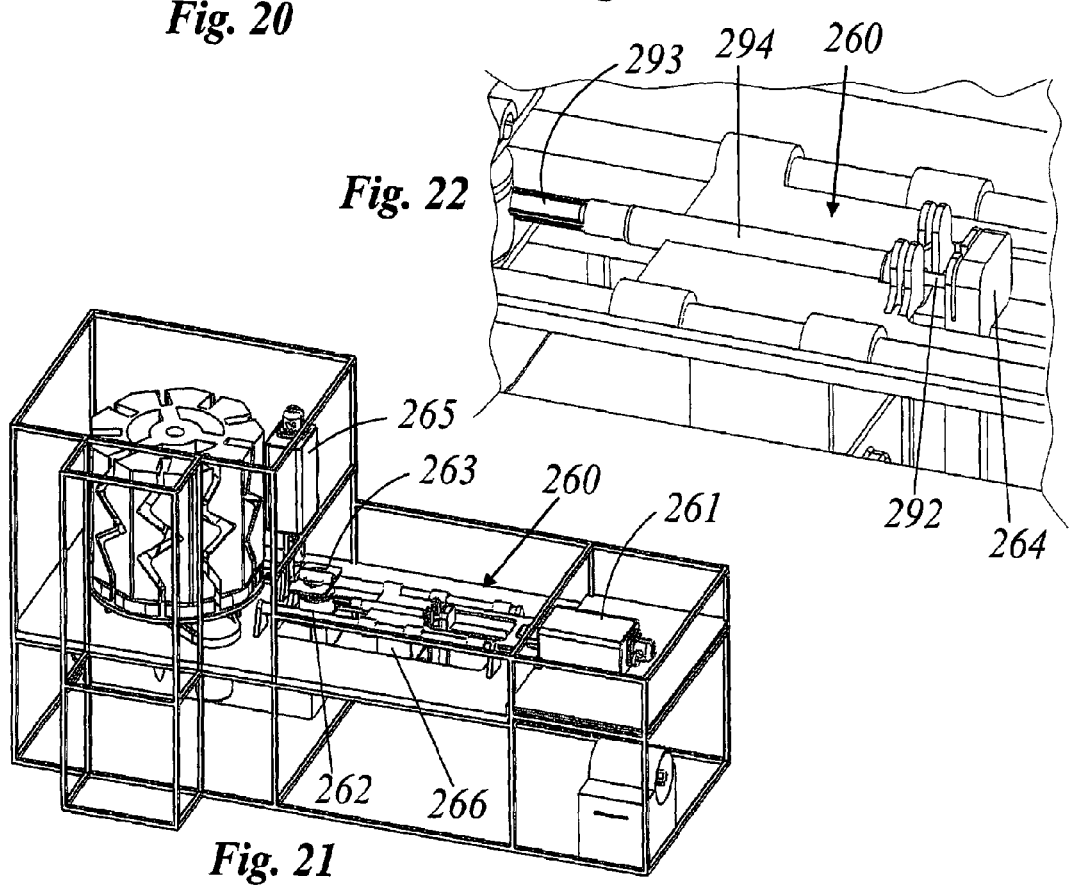
Fig. 22
Fig. 21

SYSTEM AND METHOD FOR PERSONALIZED INJECTION TREATMENT

CROSS-REFERENCE TO RELATED APPLICATIONS

The present application claims priority to U.S. Provisional Application Ser. No. 61/437,152 filed Jan. 28, 2011, which is herein incorporated by reference in its entirety.

BACKGROUND

1. Field of the Invention

The present invention relates to a system and method for personalizing an injection treatment for administering pharmaceutical agents to a patient.

2. Background of the Art

Americans are increasingly aware of the health environment, available drugs, and information technology. They demand that disease prevention and treatment should be tailored for the individual's need, where possible.

There is a greater benefit to administer injectable combinations of pharmaceutical agents such as vitamins, growth hormones, glucosamine, omega-3 fatty acids, insulin and other such agents. When a medication is administered orally, the bioavailability (i.e., the fraction of the ingested dose which is actually absorbed) of such agents significantly decreases due to incomplete absorption and first-pass metabolism, which may vary from patient to patient. However, the bioavailability of agents administered intravenously can be up to 100%. Also, it is reported that 15% of the population cannot properly absorb vitamins and other oral medications if administered orally. Moreover, since the medication requirements can vary from patient to patient, it is necessary to develop a personalized formulation of pharmaceutical agents in an injection to meet the needs of the patent.

British researchers say tumors begin to shrivel within 24 hours of injecting a vitamin E extract into patients. After ten days the tumors have almost disappeared According to Jane Higdon, Ph.D. of Oregon State University, there is currently no evidence in humans that taking oral alpha-tocopheryl succinate supplements delivers alpha-tocopheryl succinate to tissues Research has suggested that the bioavailability of Vitamin E from natural sources is twice that of synthetic sources. Furthermore, it is important to note that studies of patients with fat malabsorption have shown that vitamin E absorption requires normal digestive processes involved in the absorption of dietary fats. Linking oral vitamin E ingestion to the proper absorption of dietary fats complicates matters because the amounts and forms of fat required for optimal vitamin E absorption are unknown.

Similarly, gastrointestinal absorption of vitamin B12 depends on the presence of sufficient intrinsic factor and calcium ions. While oral absorption is considered too unreliable in patients with pernicious anemia or other conditions, an injection of vitamin B12 may prevent the progression of neurologic damage in severe cases. Parenteral administration of vitamin B12 treat a variety of conditions including pernicious anema, age related vitamin B12 deficiencies, lessens severity of Alzheimer's disease, reverse/contain cases of senile dementia, therapeutic value in treating Autism/ADD, and Multiple Sclerosis. Reportedly, 94% of children with symptomatic of autism spectrum disorders respond to Methyl-B12 therapy (vitamin B12 injections).

Various systems are known for compounding various pharmaceutical admixtures in a single container. See, e.g., U.S. Pat. Nos. 7,610,115, 7,194,336, 7,171,992, 6,975,924, 6,951,228, 5,697,407, 5,431,202, 5,085,256, 5,040,699, 4,922,975, 4,789,014, 4,653,010, 4,513,796, and 4,467,844 for various fluid transfer and compounding systems.

However, there is a significant pharmacoeconomic gap between prescription drug treatments with pharmaceutical agents and general self-care with currently available pharmaceuticals. What is needed is a system usable in a physician's office or clinic to enable a personalized treatment of patients with individually compounded admixtures of pharmaceuticals, biologics, or injectables either intravenously (IV), intramuscularly (IM) or subcutaneously. Further needed is a system incorporating the latest information technology employing, for example, wireless, software, and/or secured Internet based communication systems.

SUMMARY

An automated system for compounding pharmaceutical agents for injection treatment of a patient is provided herein. The system comprises: a housing enclosing an interior space; an inventory structure having a plurality of chambers for individually holding one or more pharmaceutical agent-containing single use capsules, wherein each capsule has a volume capacity of from about 0.1 to about 10.0 mL liquid; means for selecting capsules in accordance with predetermined pharmaceutical agents contained in said capsules; means for moving the selected capsules to a processing area; means for sequentially transferring a controlled quantity of the predetermined pharmaceutical agent with direct fluid communication from each selected capsule to a product container such as a product vial or a syringe under positive or negative pressure; and means for automatically discarding spent capsules from which the pharmaceutical agents have been removed after a single use.

This innovative technology will enable a novel personalized medicine platform where the personalized medicine opportunity can be implemented, it can be used to safely and efficiently expand physician services, improve treatment and improve outcomes. This device is applicable for patients requiring effective doses of treatment combinations of vitamins, growth hormone, glucosamine, omega-3, onabotulinumtoxin A, insulin and other agents that are used for in-office injection.

BRIEF DESCRIPTION OF THE DRAWINGS

Various embodiments are described below with reference to the drawings wherein:

FIG. 1 is a perspective view illustrating one embodiment of the invention;

FIGS. 2A-2D illustrate preparation of a product vial by mounting a connector and cap thereto;

FIG. 16 illustrates a pharmaceutical agent-containing capsule;

FIG. 17 is a perspective view illustrating the loading of the capsule into the apparatus of the invention;

FIG. 18 is a perspective view of an inventory structure;

FIG. 19 illustrates a hypodermic syringe;

FIG. 20 illustrates the loading of the hypodermic syringe into the apparatus of the invention;

FIGS. 21 and 22 illustrate the positioning of the hypodermic syringe into the syringe station;

DETAILED DESCRIPTION OF PREFERRED EMBODIMENT(S)

Figure 3A:
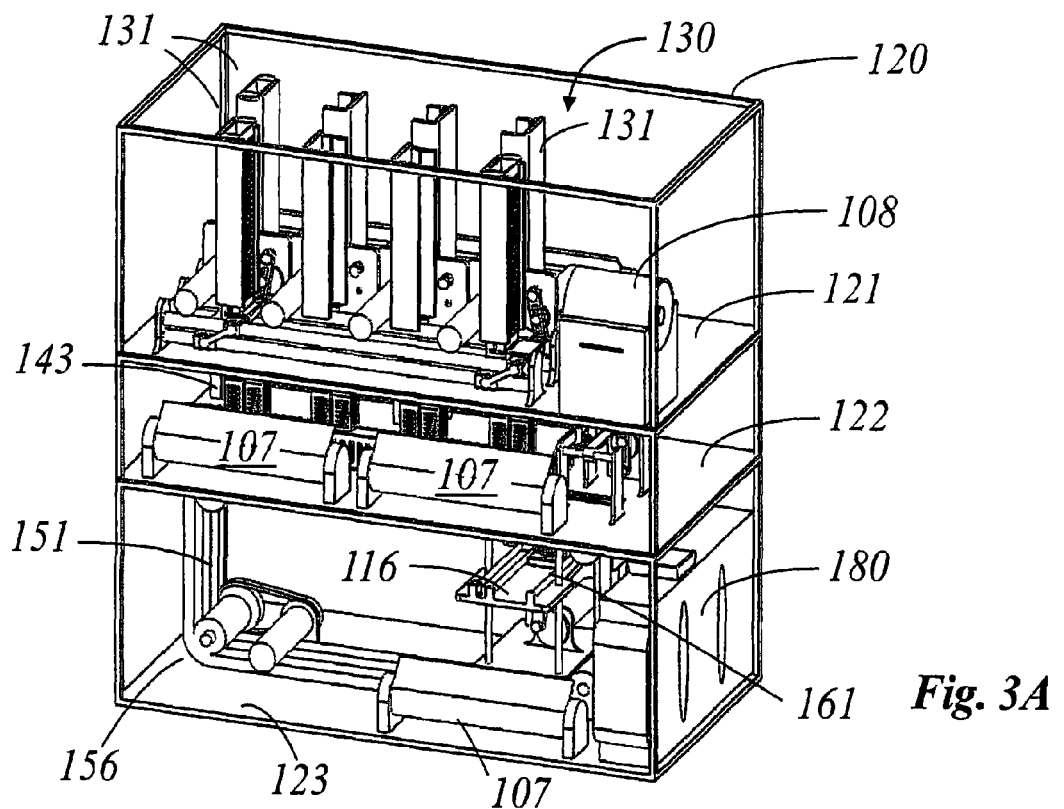
FIGS. 3A and 3B are, respectively, front and rear perspective views of the interior of the apparatus of the invention.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will also be understood that any numerical range recited herein is intended to include all sub-ranges within that range.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

This system and method for personalized injection treatment is synchronized with a complementary health management system (a computerized and networkable via wireless or wired connection) and will automatically compound and record patient specific doses of injectable medicine for disease prevention and/or treatment and the patient's progress will be monitored on the Internet longitudinally. The term herein can mean a sick or healthy human or animal (e.g., mammals such as dogs, cats, pigs, horses or cattle). The term "pharmaceutical agent" as used herein refers to an injectable solution providing health benefits and/or a therapeutic effect and or therapeutic potency including, but not limited to a vitamin, a drug, a neutraceutical, a biologic or any combination thereof The invention herein will compound the components with the customized, personalized dosage proportion, and then prepare a single product container such as a product vial or syringe for injection. The size of the invention may be similar to those gourmet single cup coffee machines or inkjet/laser printers. The proportion is determined by the physician or an Internet tool that is scientifically validated. A physician may make a personalized compounding order for injectable solutions such as vitamins, growth hormone, glucosamine, omega-3, onabotulinumtoxin A (e.g., BOTOX®) and insulin through communication devices such as a computer, a PDA, or a smart phone. Operators such as physicians or nurses may input a compounding order directly and manually with using a control pad and the system may have a control screen such LED and LCD monitor. Alternately, the system can have a touch screen unit combining display and input units. When the single product container is created, the optimizer will input the patient record into the server simultaneously. The patient may have received a set of codes in advance via an Internet tool and may bring in the print-out for the physician. An inventory structure can have a plurality of vertical chambers individually holding one or more pharmaceutical agent-containing capsules.

Each chamber can typically store 10 to 30 capsules. The capsules can have a volume capacity of about 0.1 to about 10.0 mL, preferably 0.1 mL to about 2.0 mL liquid, and most preferably about 1.0 mL liquid. The pharmaceutical agent-containing capsules and the chambers preferably will be clearly labeled and color coded. Once the pharmaceutical agent-containing capsules are loaded into the device, it will compound the exact proportion into a single injection product container. The delivery components are thoroughly sterilized and an empty product container can be loaded by an operator. The product container can have a volume capacity of about 0.1 to about 10.0 mL and typically about 2.0 mL liquid. The capsules and product container can be completely or partially filled with the pharmaceutical agent. Depending on the compounding order, the capsules can be selectively loaded and transported to a processing area. At the processing area, the selected capsules can be connected to the product container and a quantity of the predetermined pharmaceutical agent can be transferred to the product container under positive or negative pressure. The positive pressure can be generated by mechanical compress outside the selected capsules and the negative pressure inside the selected capsules can be employed by a vacuum pump or syringe in order to draw the pharmaceutical agent out of the capsule. Alternatively, the capsules can be properly pressurized and packaged so that inside solution may automatically come out without auxiliary pressurization. The transferring quantity can be controlled by regulating amount of the applied pressure and time. The consumed medicine capsules are disposed of automatically after a single use. The solution inside the capsules can be transferred through a connector, which is pre-assembled with a product vial as a cap before it is placed into the system and consisted of a needle and an air vent. Alternatively, the solution can be transferred through an extraction needle engaged with the loaded capsules and an injection system engaged with the product vial. The system may be enclosed by a housing and an air ventilation system may be included in the apparatus. All of the embodiments described below can include sterilization means such as UV lamps to provide an internal aseptic environment. A plurality sensors such as proximity sensors, distance sensors, and temperature sensors may be placed in order to monitor if desired capsules are loaded, in order to monitor if the system operates properly in order to check if the gate/door is closed, and also in order to monitor temperature inside the system. Sensors can be used in each of the embodiments described below and are commercially available, for example, from Sharp in Japan, Keyence Corporation of America in Itasca, Ill., Automation Direct in the U.S., and c3 controls in the U.S. After all processes are completed, the product container can be taken out by an operator. Labels which include patient information and compounding order with text, bar code, or QR code format, can be printed out and the labels will be attached on the product container and the patient chart.

Referring now to FIGS. 1 to 13B, an embodiment of the system apparatus 100 of the invention for compounding pharmaceutical agents is illustrated.

FIG. 1 illustrates a housing 110 having a top surface with a lid 111 for allowing access for loading pharmaceutical agent-containing capsules into the system apparatus. The housing 110 includes a liquid crystal display (LCD) screen 112 on a front wall for providing information to the user as to the status and operation of the system. The front wall can also include a key pad 113 for data entry and the input of operating instructions. Alternatively, the system apparatus 100, as well as the embodiments described below, can include touch screens which include functions of information display and input of instructions/information. A side surface also includes a door 114 for a label printer, the printed label being issued from slot 115 on the front wall of the housing. Vial loading door 119 provides access for loading an empty product vial into a product vial chamber 116 and removal of the filled product vial therefrom. Door 117 provides access to a spent capsule disposal bin for removal from the system apparatus. Electrical components and microprocessor(s) are contained in the rear sections 118 of the apparatus 100 which can be opened to provide access thereto.

The invention includes a system also responsive to instructions provided remotely by computer/PDA/smart phones and the like by cable, Bluetooth, or internet protocol/ transmission control protocol (IP/TCP). Such instructions relate to the type and amounts of pharmaceutical agents are to be compounded for the patent as well as appropriate patient information.

Referring now to FIGS. 2A-2D a product vial 103 having a liquid volume capacity of preferably about 2.0 mL, is prepared for filling by attachment thereto of a connector cap 170. The connector cap includes a needle 171 and an air vent 172 and seals the top 104 of the product vial 103. The pharmaceutical agents are compounded in the product vial 103 which is then used for injection treatment of a patient. A protective cap 175 is mounted to the connector cap 170 after the product vial has been loaded with pharmaceutical agent to prevent accidental needle stabs in handling the product vial 103. The connector cap 170 includes an access port 173 through which a hypodermic syringe needle can be inserted to load the pharmaceutical agent composition onto the hypodermic syringe for subsequent injection into a patient. Protective cap 175 has a similar access port 176. The access ports 173 and 176 include a resilient material such as rubber, which is penetrable by the hypodermic needle, but which seals the port after withdrawal of the hypodermic needle.

Figure 3B:
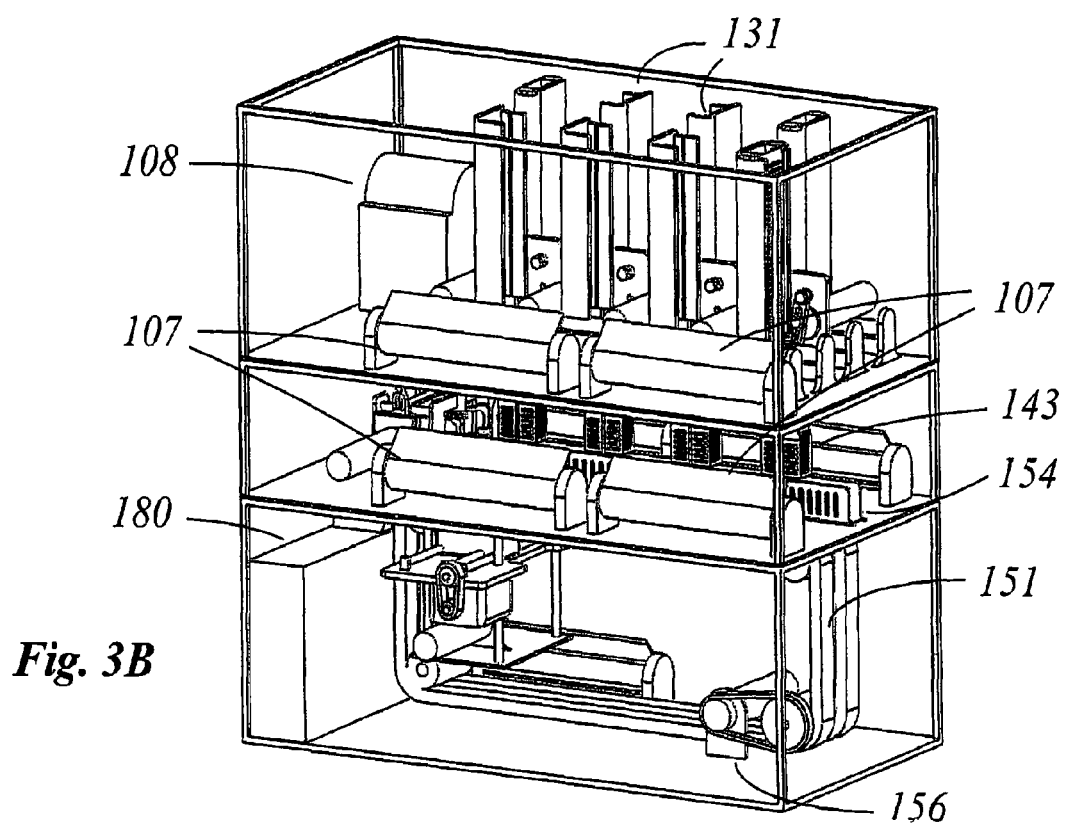
Figures 4, 5:
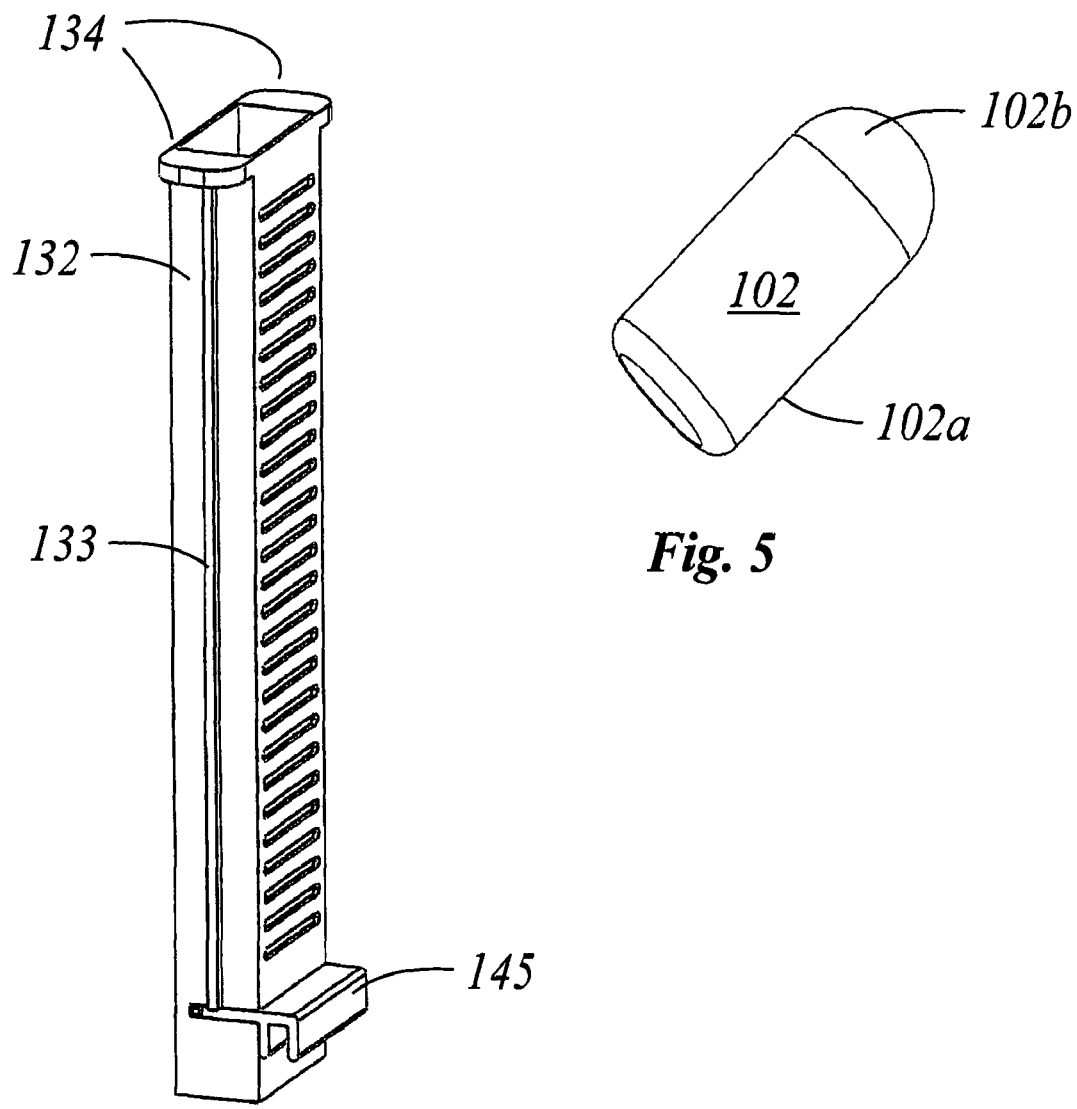
FIG. 4 is a perspective view of a channel member.
FIG. 5 illustrates a pharmaceutical agent-containing capsule.

Referring now to FIGS. 3A-3B, in an embodiment of the invention frame 120 surrounds and supports the internal mechanism of the system apparatus 100. Frame 120 can be fabricated from metals such as ferrous alloys or aluminum, or engineering plastics such as, for example, acrylonitrile butadiene styrene (ABS), polycarbonates (PC), polyamides (PA), polybutylene terephthalate (PBT), polyethylene terephthalate (PET), polyphenylene oxide (PPO), polysulphone (PSU), polyetherketone (PEK), polyetheretherketone (PEEK), polyimides, polyphenylene sulfide (PPS), and polyoxymethylene plastic (POM). Upper, middle and lower levels of the apparatus are at least partially delimited or defined by upper platform 121, middle platform 122 and lower platform 123. An inventory structure 130 is supported on upper platform 121 as well as a label printer 108 and UV lamps 107 for sterilization of the environment. Temperature sensors (not shown in the figure) can be placed inside the system in order to monitor if the system is over heated. The inventory structure includes a plurality of chambers such as vertical racks 131 in parallel arrangement. The racks each include a linear interior space adapted to slidably receive a corresponding channel member 132 (FIG. 4). The channel members 132 are each adapted to receive and store a plurality of pharmaceutical agent-containing capsules 102 (FIG. 5). Capsules 102 each have a cylindrical body 102a and a hemispheric end portion 102b, and are fabricated from a flexible polymeric material which can be punctured by a needle but which is strong enough to withstand normal handling stresses without breaking or fracturing, and preventing tear propagation and leaking after puncture. The capsules 102, racks 131 and/or channel members 132 can be color coded or identified by bar codes so that the proper pharmaceutical agents are loaded into the racks 131. The channel members 132 each include an elongated body having side rails 133 configured to slidably engage corresponding linear notches in the interior side surfaces of the racks 131. The channel members 132 also include laterally extending wings 134 at the top of the body to facility grasping by a user's fingers. A capsule separation system 141 described below engages a slot in the bottom portion of each channel member 132.

Figure 6:
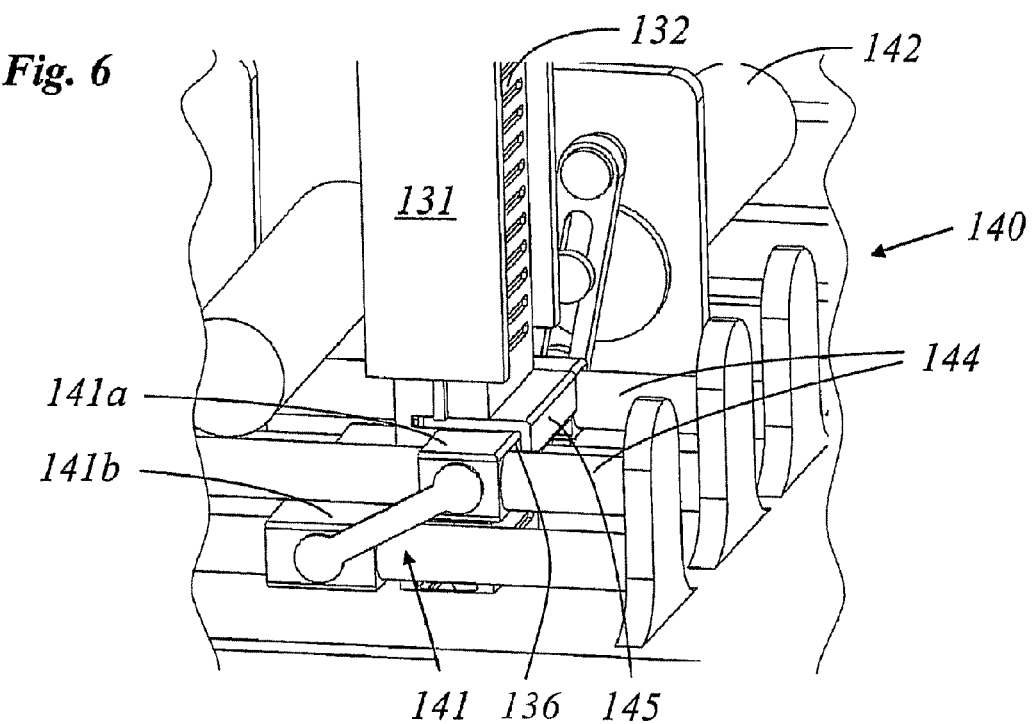
FIGS. 6 and 7 illustrate, respectively, the movement of a sliding gate 141 at the bottom of the channel member to release a capsule from the bottom of the channel member.
Figure 7:
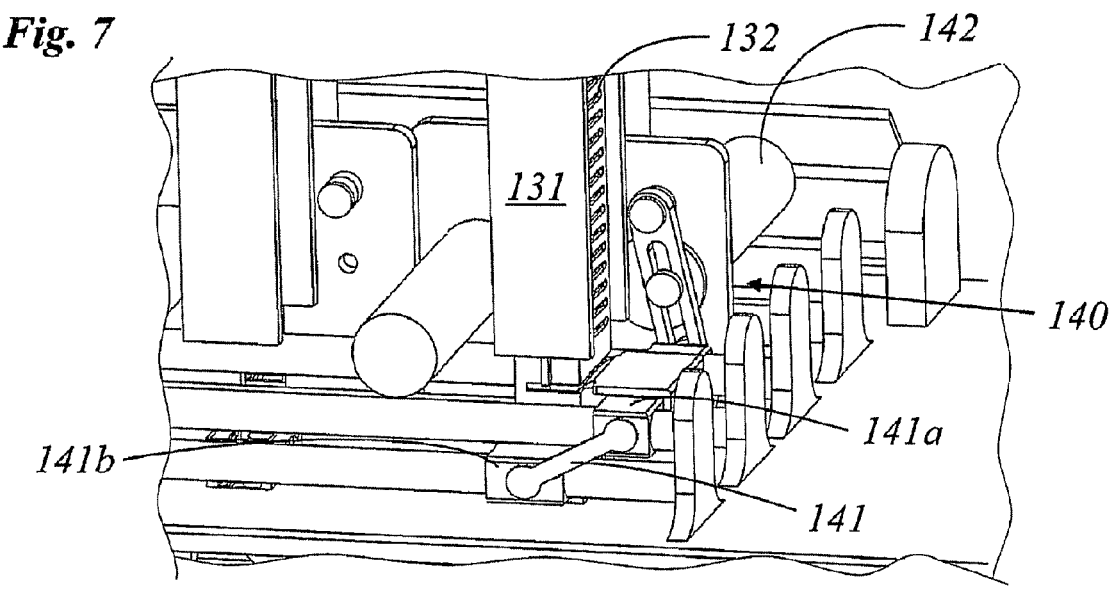

Referring to FIGS. 6 and 7, the system apparatus 100 includes means for selecting capsules in accordance with the pharmaceutical agents contained therein. The selection means 140 include a capsule separation system 141, and a motor 142 for moving the capsule separation system 141. The capsule separation system includes upper gate 141a and lower gate 141b slidably movable along guide rails 144. The separation system 141 further includes a blocking plate 145 mounted to the upper gate 141a and slidably movable in and out of slot 136 in the channel member 132. The capsule separation system is slidably movable between a first position in which the upper panel blocking plate 145 is fully engaged with the slot 136 in the respective channel member 132 so as to prevent any capsules 102 from exiting the channel member 132 from the bottom thereof (FIG. 6), and a second position wherein the blocking plate 145 is moved outside of the slot 136 in the channel member 132. However, in the second position the lower gate 141b is moved below the bottom of the channel member 132 to prevent the capsule from dropping further. The capsule separation system 141 is then moved back to the first position and the selected capsule 102 is allowed to exit the bottom of the channel member 132, but the blocking plate 145 is now in the first position which prevents another capsule from moving lower. The space between the blocking plate 145 and the lower gate 141b accommodates only a single capsule. Accordingly the back and forth motion of capsule separation system 141 limits the exiting of the capsules 102 from the bottom of the channel member 132 to one capsule at a time. Motor 142 moves gate 141 in response to instructions for selecting the pharmaceutical agent contained in the capsules 102 loaded in the rack 131. The operation of the motor 142 is adjusted to permit only a single capsule 102 to be released at a time. The released capsule 102 then falls into a chute 143 which directs the capsule 102 onto a linear transport system as described below. Each rack 131 includes its own motor and capsule separation system.

Figure 8:
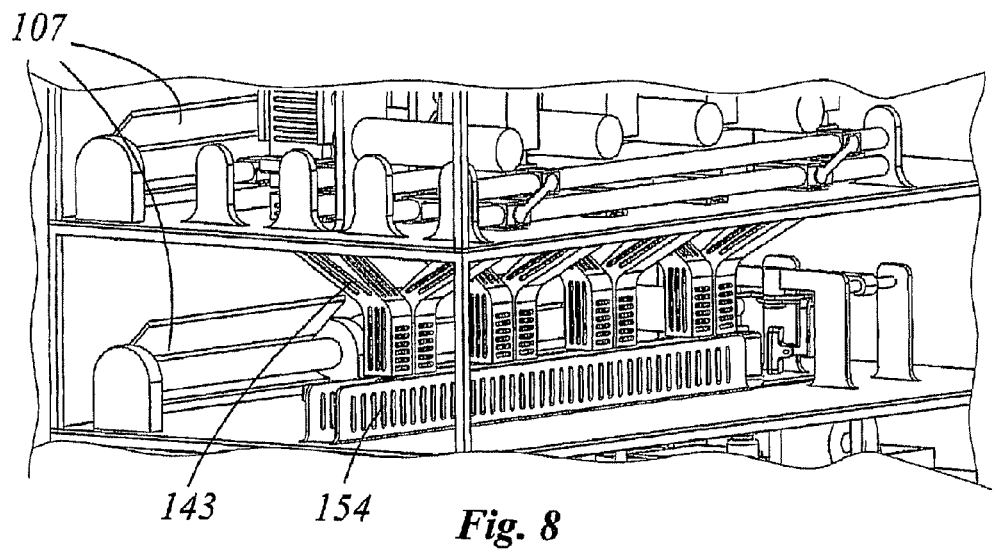
FIGS. 8 and 9 are interior perspective views illustrating the conveyor means for moving capsules into a processing area.
Figure 9:
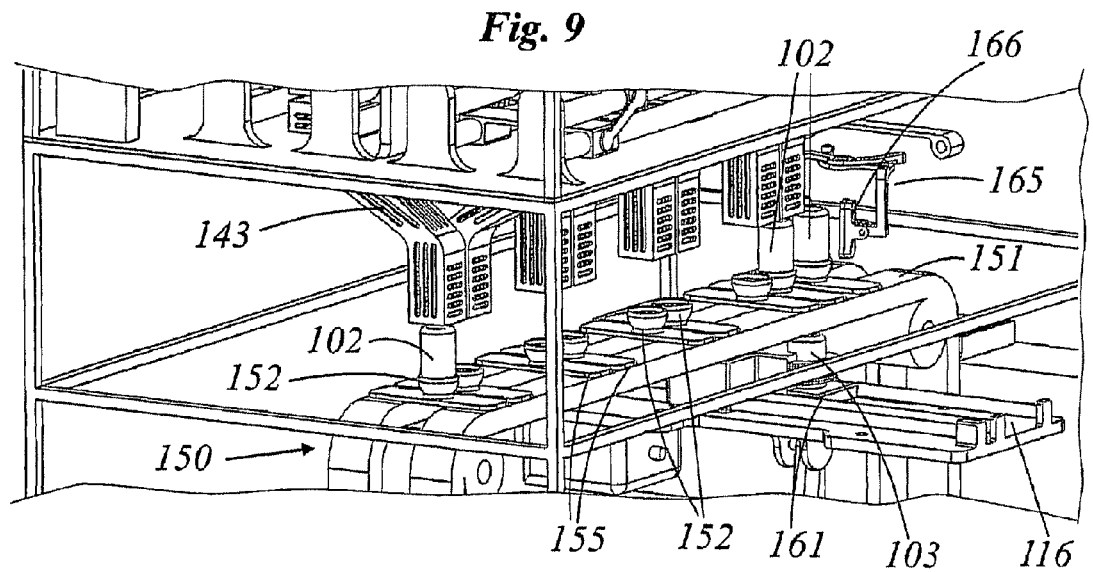

Referring to FIGS. 8 and 9, the system 100 includes a linear transport system 150 as means for moving the capsules 102 to a processing area, said means including a chute 153 associated with each rack 131, a conveyor belt or chain 151 and capsule holders 152 fixedly mounted to respective saddling plates 155, which are in turn mounted to the conveyor belt/chain 151, and also a linear actuator 156 (FIGS. 3A and 3B). Each capsule 102 is dropped through a respective chute 143 into a respective capsule holder 152 having a hemispheric cavity to accommodate the hemispheric end 102b of the capsule, which is then linearly moved to a processing area in which the capsules 102 are individually punctured and compressed to force the liquid contents of the capsules 102 into the product vial 103. Guide channel 154 (FIG. 8) maintains the capsules in the proper orientation and position while being moved.

Figure 10A:
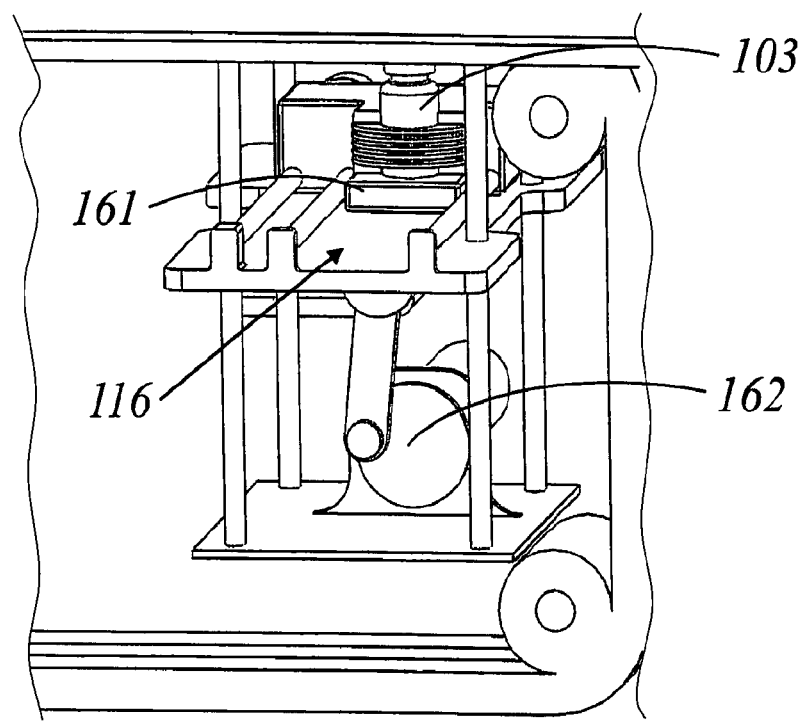
FIGS. 10A and 10B are perspective views of the means for puncturing the capsule which include a movable platform for raising the product vial with attached connector from a lower position (FIG. 10A) to an upper position (FIG. 10B) wherein the needle of the connector cap pierces the pharmaceutical agent-containing capsule
Figure 10B:
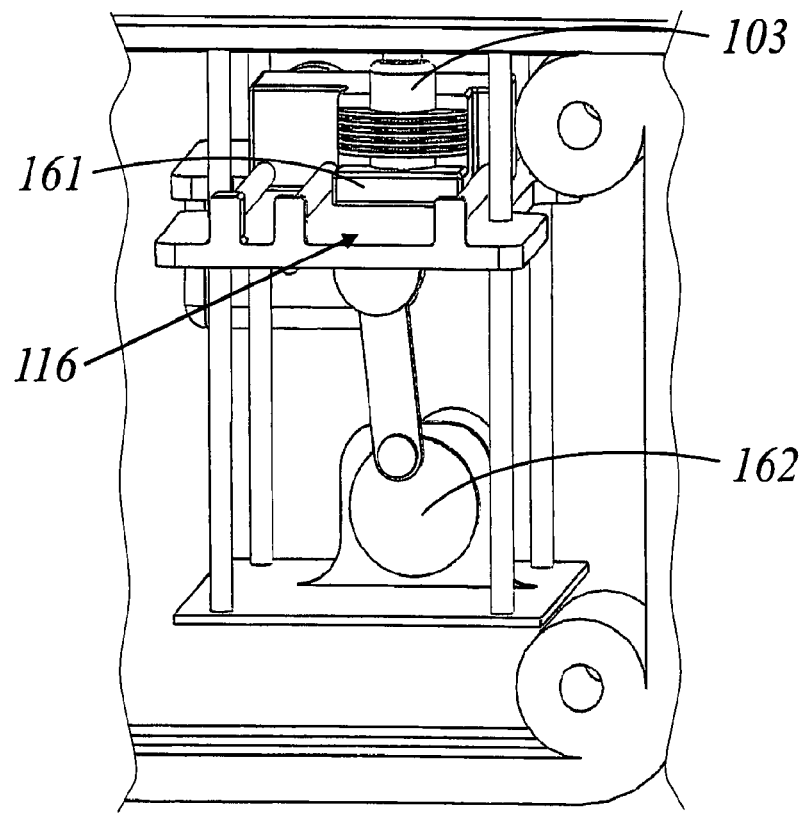

Referring to FIGS. 10A and 10B, the processing area includes means for puncturing the capsules 102 and means for transferring a quantity of the pharmaceutical agent from the capsule to the product vial 103.

More specifically, the puncturing of the capsule 102 is accomplished by loading the product vial 103 with the connector cap 170 attached thereto into a product vial chamber 116 and onto a product vial loading platform 161. The loading platform 161 is then laterally moved to align the product vial 103 with the capsule 102. A motorized cranking member 162, in response to appropriate operating instructions, lifts the product vial 103 vertically upward until the needle 171 punctures the end 102b of the capsule 102, thereby permitting fluid communication therewith.

Figure 11:
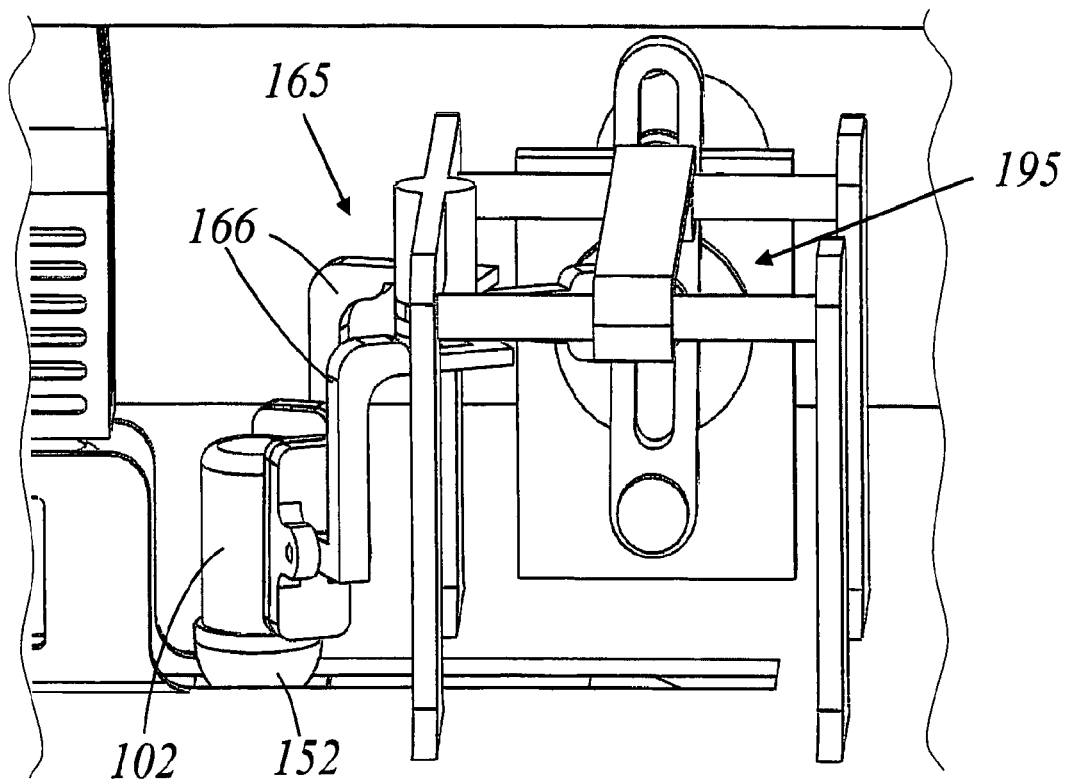
FIG. 11 illustrates caliper means for applying positive outside pressure to compress the capsule and force pharmaceutical agent into the processing vial.
Figure 12:
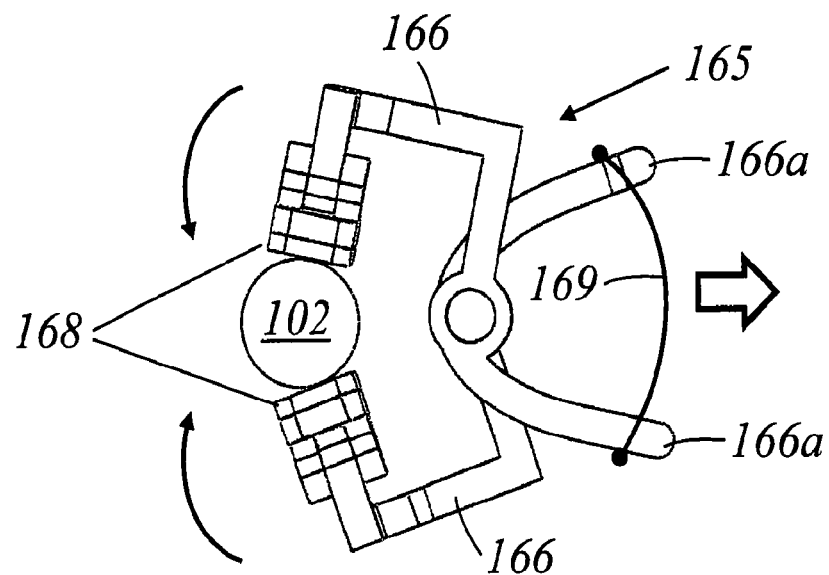
FIG. 12 is a plan view of the caliper and capsule.

Referring to FIGS. 11 and 12, the means for transferring the pharmaceutical agent from the capsule 102 to the product vial 103 includes calipers 165 having jaws 166 movable between an open position to a closed position in response to appropriate operating instructions. The jaws 166 each have a soft pad 168, which contacts the capsule 102. Cable 169 can be connected to arms 166a and when pulled by motor 195 as shown by the arrow, cable 169 closes the jaws 166. In the closed position the jaws apply external pressure to the side 102a of capsule 102, which forces fluid pharmaceutical agent through the bore of needle 171 and into the product vial 103. A quantity of the transferred solution can be determined by controlling the applied external pressure, which is regulated by pulling force or distance of the cable 169. Vent 172 in the connector cap 170 permits air to escape from the product vial 103 as it is being filled. After the processing of a capsule containing one pharmaceutical agent is completed another capsule containing another pharmaceutical agent is moved into the processing area for the same procedure until all of the selected pharmaceutical agents have been compounded.

Figure 13A:
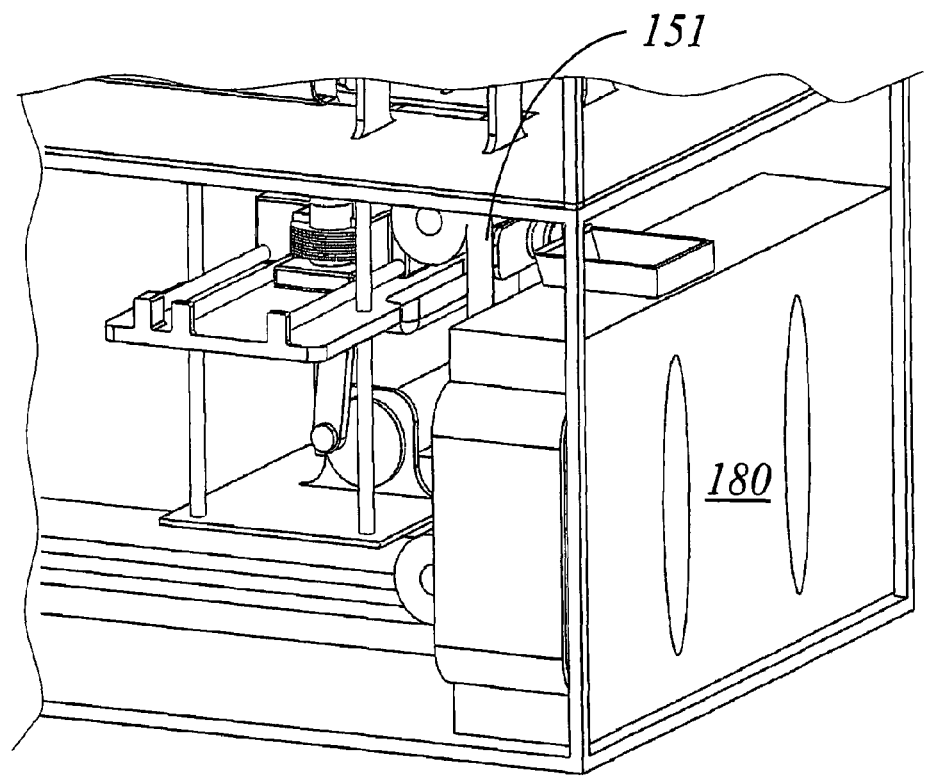
FIGS. 13A and 13B are, respectively, perspective and elevational views illustrating the disposal of the spent capsule into the discard bin.
Figure 13B:
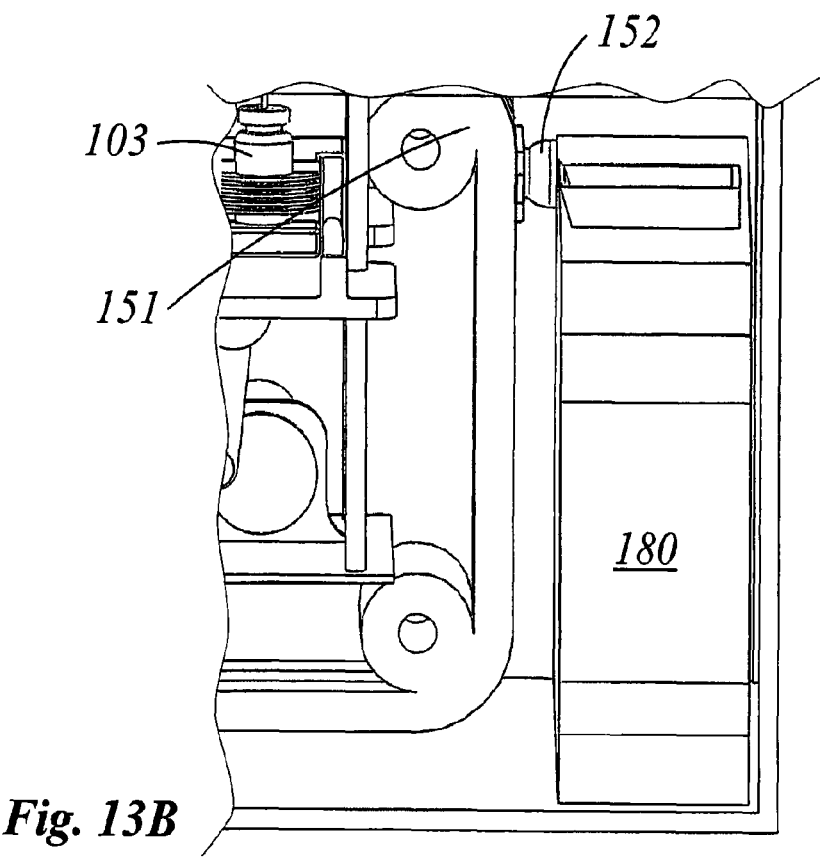

Referring to FIGS. 13A and 13B, the system includes means for automatically discarding the spent capsules 102, which includes a spent capsule waste bin 180 positioned at an end of the processing area. The conveyor belt 151 advances the spent capsule to the end of the conveyor system 150 wherein the belt turns downward and the spent capsule is dropped into the bin 180. The bin 180 can later be removed from the system apparatus 100 through the capsule disposal door 117. Accordingly, each capsule 102 is discarded after a single use.

Referring now to FIGS. 14A to 27, another embodiment 200 of the invention is shown. In this embodiment the product container is a hypodermic syringe, which optionally may be used directly for injection.

Figure 14A:
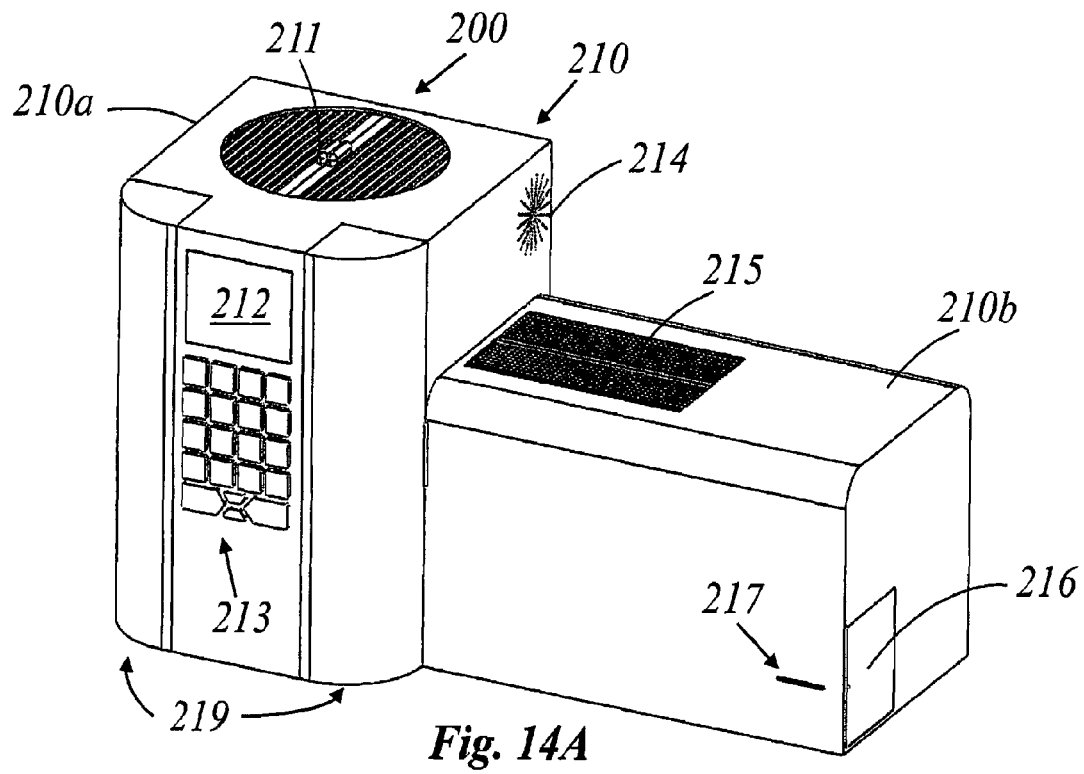
FIGS. 14 A and 14B are perspective views of another embodiment of the invention.
Figure 14B:
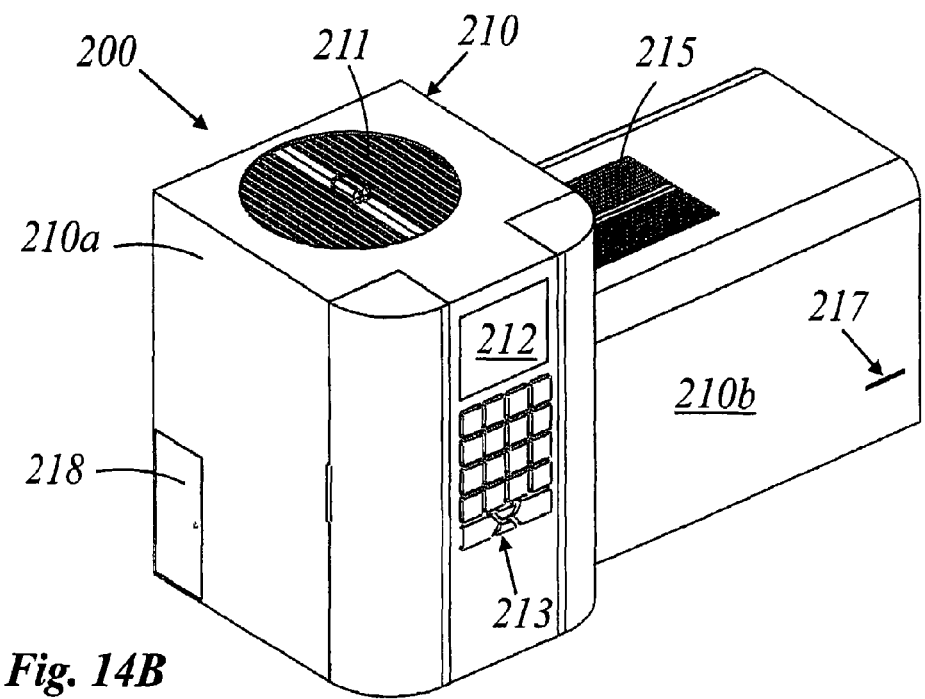

Referring more specifically now to FIGS. 14 A and 14B, housing 210 includes two parts: housing portion 210a and housing portion 210b. Housing portion 210a includes a lid 211 on its upper surface for capsule loading, LCD display 212 and keypad 213 on the front surface, a vent 214 and a door 218 for spent capsule disposal. Housing portion 210a also includes sections 219 in which the electrical components and microprocessor(s) are situated. Sections 219 can be opened to provide access to the system electronics. Housing section 210b extends laterally from a side of housing section 210a and includes a lid 215 for loading a hypodermic syringe, a door 216 for a label printer 270 (FIG. 15), and a slot 217 for printed labels.

Figure 15:
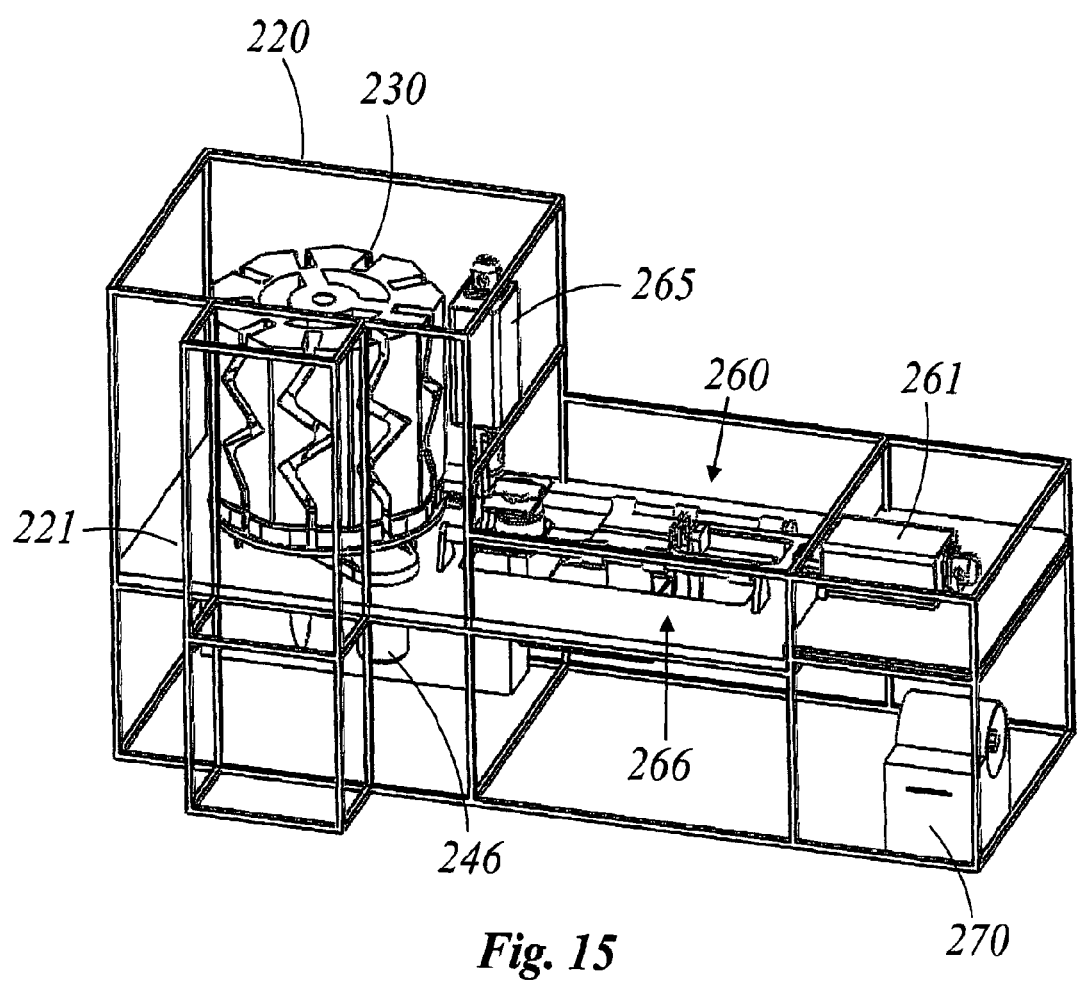
FIG. 15 is an interior view of the embodiment of FIGS. 14A and 14B.

Referring to FIG. 15, system apparatus 200 includes a frame 220 and a platform 221 for supporting the components described below.

Referring also now to FIGS. 16 to 18, in the housing portion 210a there is positioned the inventory structure 230 which comprises a non-movable carousel body 231 having a plurality of chambers 232 arranged around a circumferential periphery of the carousel body 231 and extending from the top of the carousel body 231 to the bottom. The chambers 232 are each adapted to hold a plurality of pharmaceutical agent-containing capsules 202 in a top to bottom array. The capsules each have a prolate body portion 203 fabricated from a sturdy plastic, which may be either flexible or rigid. However, the end 204 of the capsule is configured with a resilient film such as rubber adapted to be easily penetrated by a hypodermic needle so as to permit transfer of the pharmaceutical agent from the capsule 202 to a hypodermic syringe. The chambers 232 are radially oriented and configured to hold elongated capsules in a lateral orientation such that the ends 204 of the capsules face radially outward. The chambers 232 can have a linear and/or zig-zag configuration. The zig-zag configuration allows for the storage of more capsules than the linear shape and provides for greater control of the movement of the capsules. In an embodiment as shown in FIG. 18 the channels 232 are zig-zag shaped.

Figure 23:
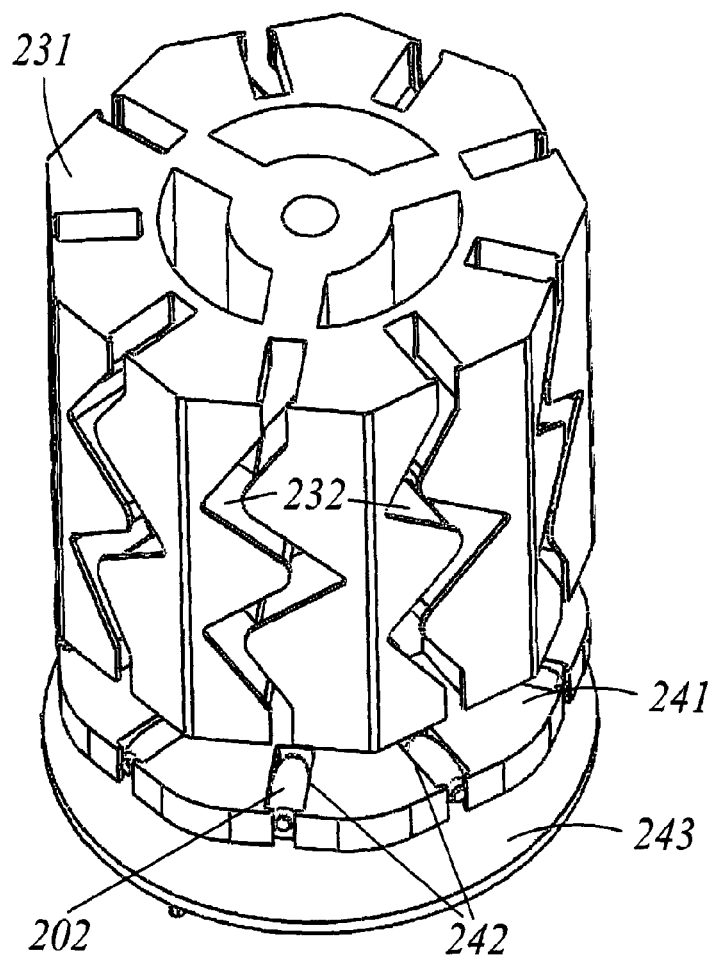
FIGS. 23 and 24 illustrate the arrangement of the carousel, working cylinder, and blocking plate.
Figure 24:
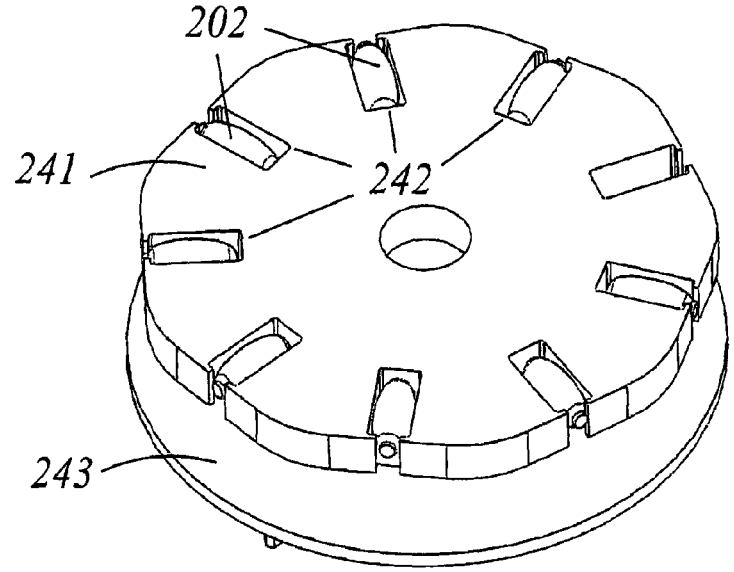

Referring to FIG. 23, beneath the carousel body 231 is a working cylindrical plate 241 having a plurality of notches 242 disposed around the circumferential periphery of the plate 241, each notch 242 being configured and dimensioned to hold a single capsule 202 in a radial configuration. The notches 242 can be aligned with channels 231 to permit the bottommost capsule 202 in a channel to drop into a corresponding notch. The working cylindrical plate is rotatable and adapted move selected capsules into a processing area as described below. The capsules can roll or slide on the blocking plate 243 below the working cylindrical plate 241 as the working plate 241 rotates.

Referring to FIGS. 23, 24, 26 and 27, beneath the working cylindrical plate 241 is a preferably non-rotatable blocking plate 243 which prevents the capsules 202 in the notches 242 from dropping out of the notches. However, the blocking plate 243 includes a gate 244, which is movable between a closed position and an open position. When gate 244 is in the open position and a notch 242 is aligned with the gate 244, any capsule in the notch is allowed to drop through the gate and into the spent capsule discard bin 280. Accordingly, after the pharmaceutical agent has been drawn out of a capsule, the working plate is rotated to move the notch with the spent capsule into alignment with the gate 244, the gate 244 is then opened and the spent capsule is discarded into the spent capsule discard bin 280 for subsequent removal from the system apparatus 200. A motor 246 positioned beneath platform 221 in the housing portion 210a (FIG. 15) rotates the working cylindrical plate 241 in response to operating instructions.

Figure 25A:
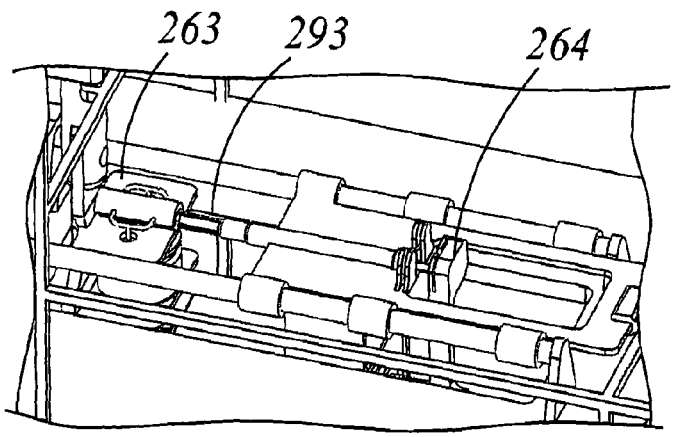
FIGS. 25A to 25G illustrate the removal of as cap from a hypodermic syringe, the puncturing of the capsule and loading of the hypodermic syringe with the pharmaceutical agent.
Figure 25B:
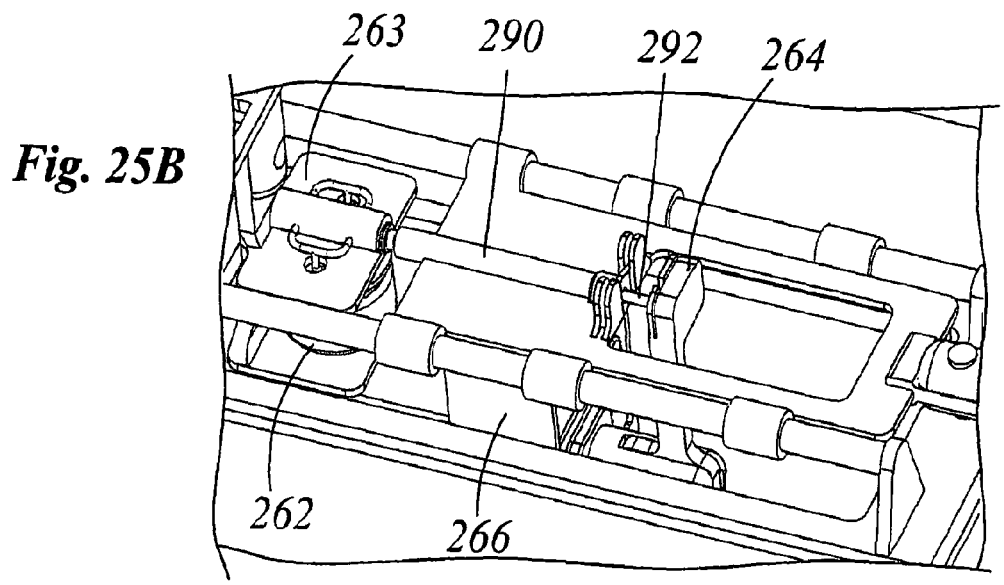
Figure 25C:
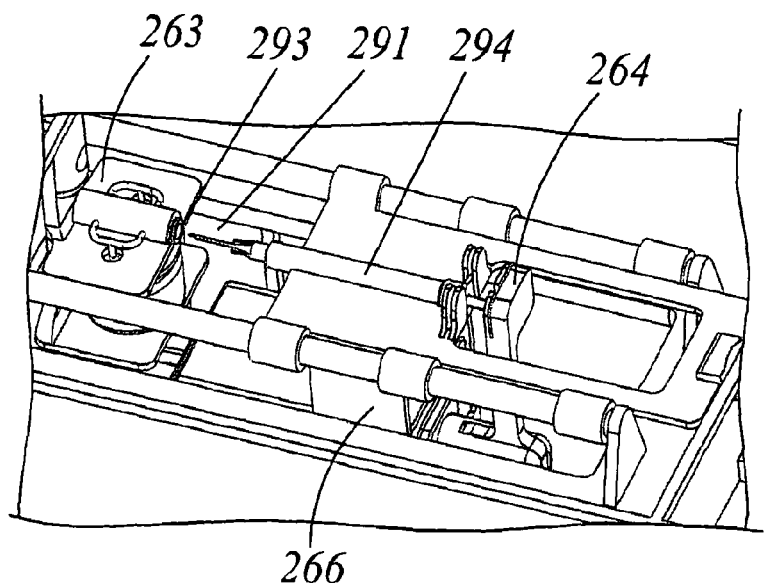
Figure 25D:
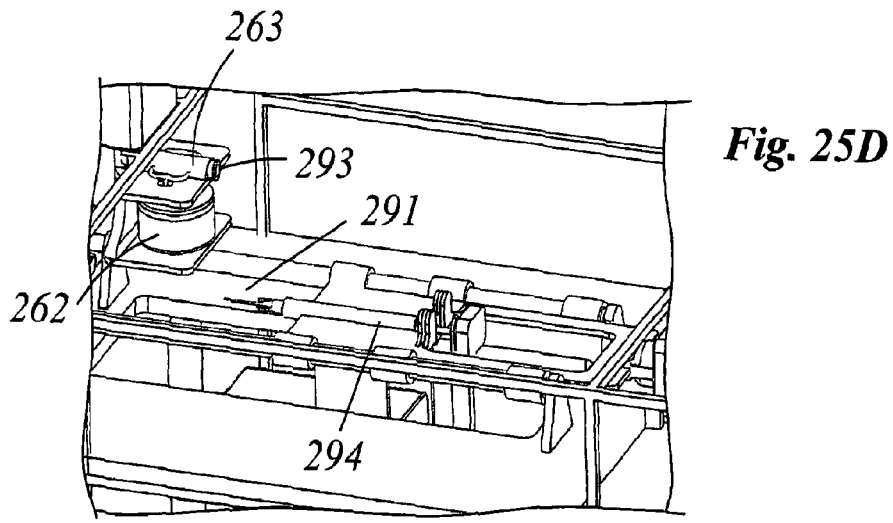
Figure 25E:
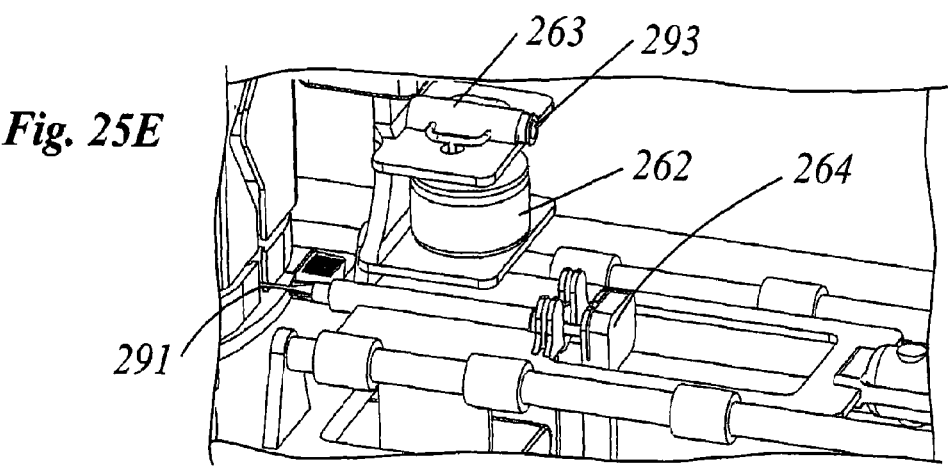
Figure 25F:
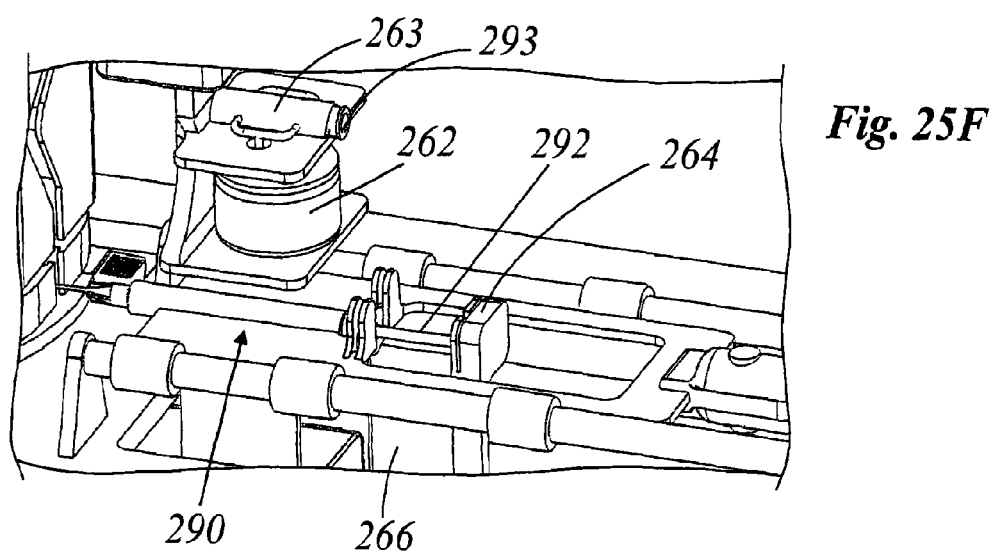
Figure 25G:
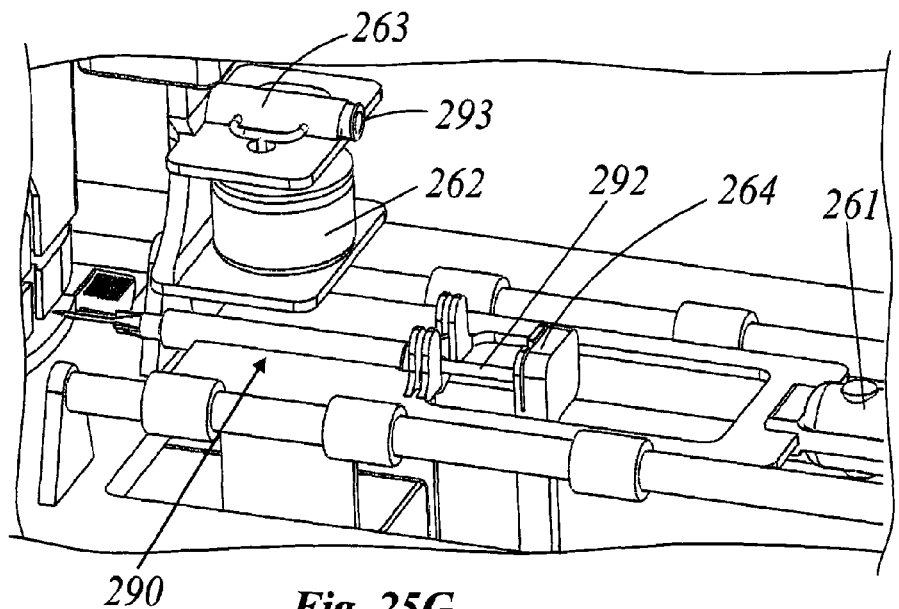
Figure 26:
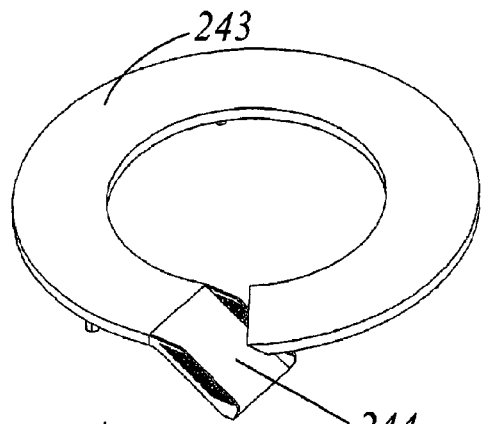
FIG. 26 illustrates the blocking plate with an open gate.
Figure 27:
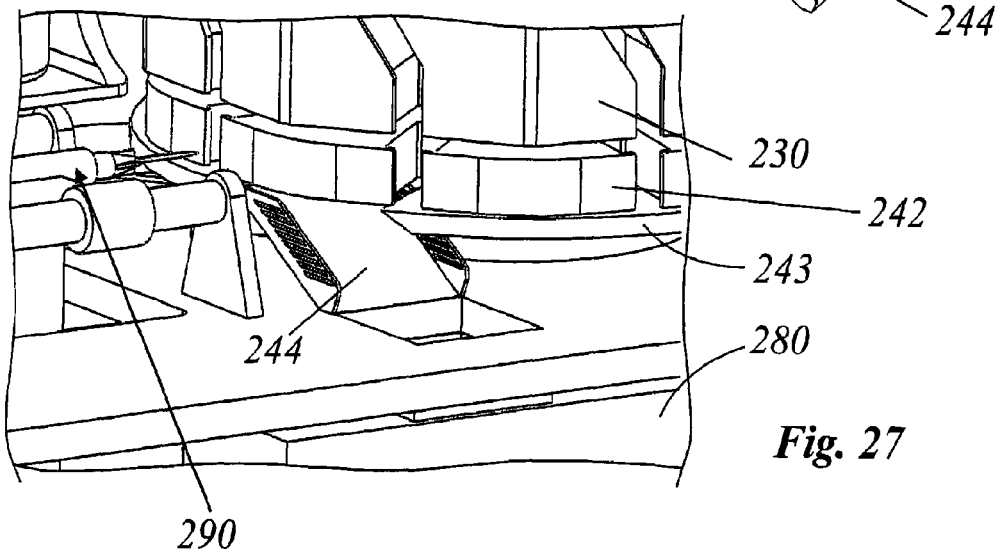
FIG. 27 illustrates the blocking plate with open gate arranged for the disposal of a spent capsule into the spent capsule discard bin.

Referring also to FIGS. 19 to 22, housing portion 210b includes means for puncturing the capsules and drawing off the pharmaceutical agent therefrom. In particular, hypodermic syringe support frame 260 is adapted to receive and move a hypodermic syringe 290 as well as to operate the hypodermic syringe so as to draw pharmaceutical agent directly from the capsule into the syringe chamber 294. The syringe 290 initially has a protective cap 293 covering the hypodermic needle 291 to prevent accidental needle sticks (FIG. 19). Referring also now to FIGS. 25A to 25G, the syringe 290 is first loaded into the support frame 260 such that the syringe chamber 294 is secured in the support frame 160 and the end of the syringe plunger 292 is engaged in the plunger grasper 264. The hypodermic syringe support frame 260 is then moved forward by a first linear actuator 261 from a first loading position to a second position wherein a cap remover 263 engages and holds the protective cap 293 (FIG. 25B). A solenoid 262 actuates the clasping mechanism of the cap remover 263 to releasably lock the cap 293. The linear actuator 261 then moves the hypodermic syringe 290 in a reverse direction to a third position to disengage the protective cap 293 from the hypodermic syringe 290 (FIG. 25C). The cap remover 263 is then moved upward by a second linear actuator 265 such that it is no longer in the way of further advancement of the hypodermic syringe 290 advancement (FIG. 25D). The first linear actuator 261 then advances the hypodermic syringe to a fourth position where the hypodermic needle punctures the end 204 of the pharmaceutical agent-containing capsule 202 in the processing area (FIG. 25E). The plunger grasper 264 is then moved backwards by a third linear actuator 266 to create a negative pressure in the syringe chamber 294, thereby drawing pharmaceutical agent from the capsule 202 and into the hypodermic syringe 290 (FIG. 25F). A quantity of the transferred solution can be controlled by travelling distance of the plunger 292 considering volume of the loaded syringe chamber 294. The first linear actuator 261 then moves the hypodermic syringe 290 backwards to a fifth position to withdraw the needle 291 from the processing area. Referring also now to FIG. 27, the working plate 241 is then rotated to position the spent capsule 202 over the gate 244, which is then opened to drop the spent capsule into the discard bin 280. If another capsule is to be used the working cylindrical plate 241 is then moved to position the new capsule in the processing area for puncture by the hypodermic needle 291 and the above described procedure is repeated. If no further capsules are to be used, the cap holder 263 is dropped down to a position wherein the protective cap 293 in alignment with the needle 291. The hypodermic syringe is then advanced again to engage the protective cap 293 with the hypodermic needle 291, the protective cap 293 is then released, and the first linear actuator moves the entire hypodermic syringe 290 backwards. The user can then remove the loaded hypodermic syringe, which is prepared for injection treatment of a patient. The label printer 270 can print out a label to be associated with the hypodermic syringe 290 to identify the contents of the hypodermic syringe 290, the patient, and any other appropriate information. The information can be printed out as text, bar code or quick response (qr) code.

Referring now to FIGS. 28 to 34B, another embodiment 300 of the invention is shown.

Figure 28:
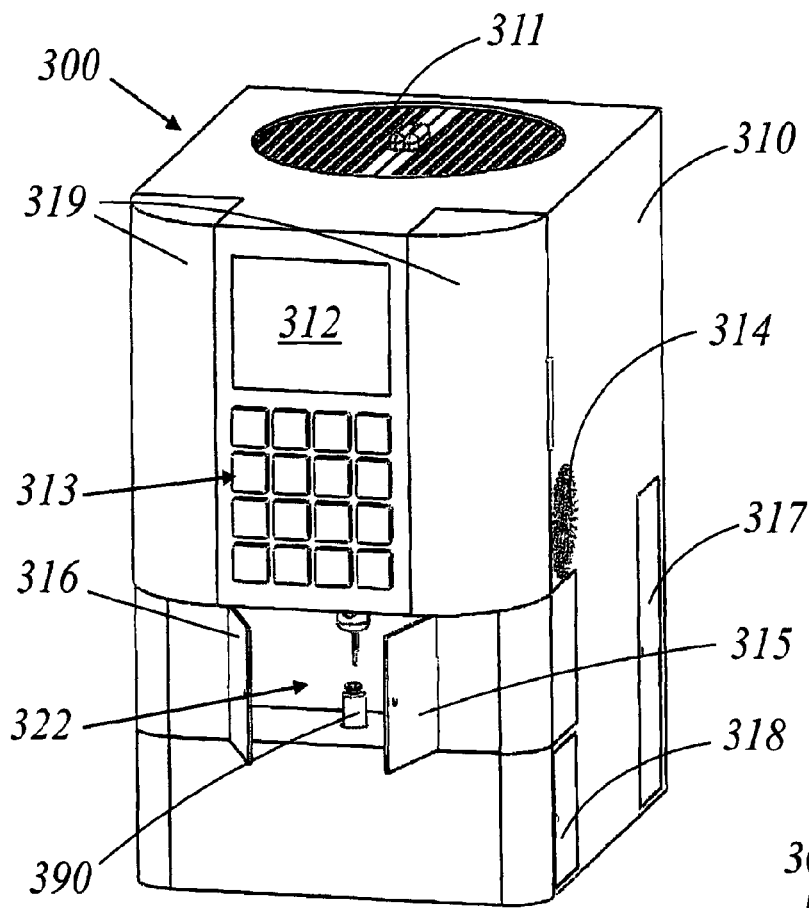
FIG. 28 is a perspective view of another embodiment of the system apparatus of the invention.
Figure 34A:
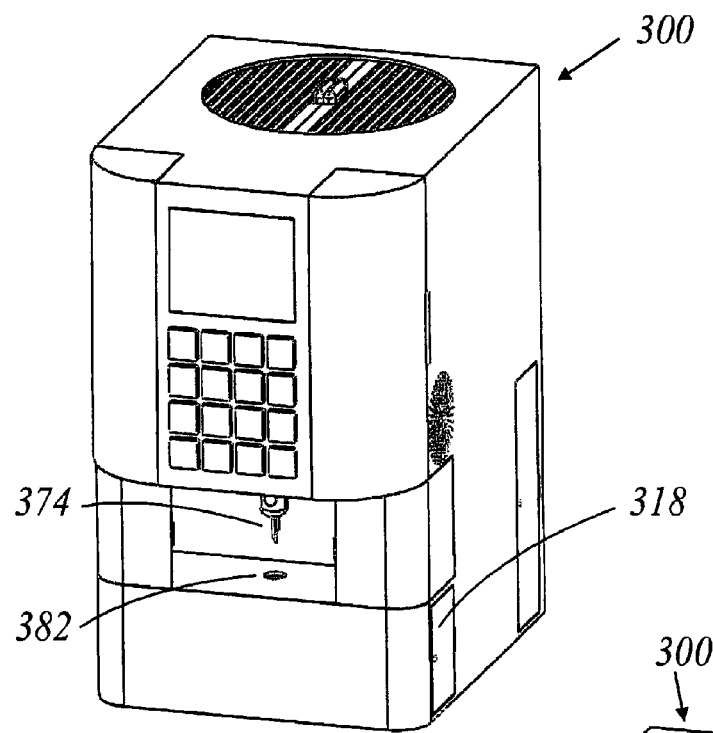
FIGS. 34A and 34B illustrate the disposal of waste solution.

Referring more specifically to FIG. 28, housing 310 includes a lid 311 on its upper surface for capsule loading, LCD display 312 and keypad 313 on the front surface, a vent 314, a door 317 for spent capsule disposal, a door 318 for waste solution disposal, a transparent cover wall 315, and doors 316 for providing access to an internal chamber 322 for placement of the product vial 390. The product vial 390 is placed in chamber 322 over a fluid drain 382 for spent fluid (FIG. 34A). Housing 310 also includes openable sections 319 in which the electrical components and microprocessor(s) are situated.

Figure 30:
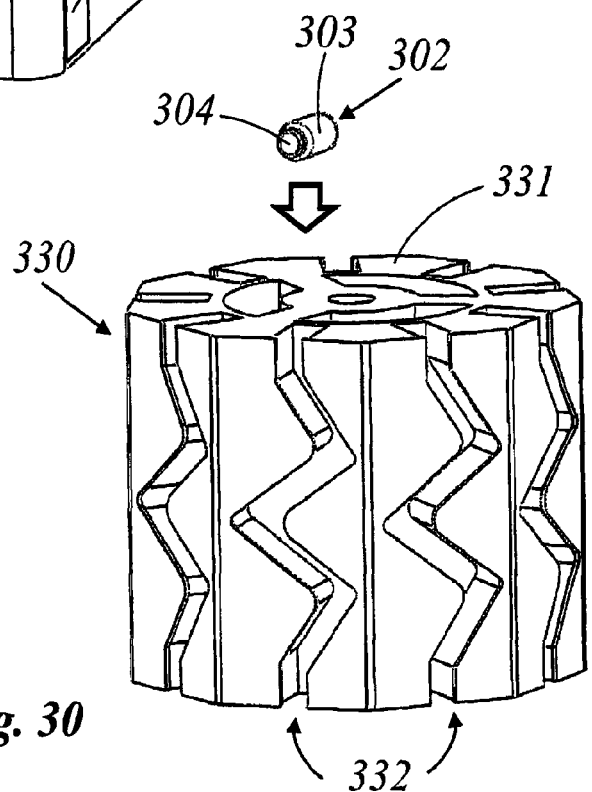
FIG. 30 illustrates the loading of a capsule into the carousel.
Figure 29A:
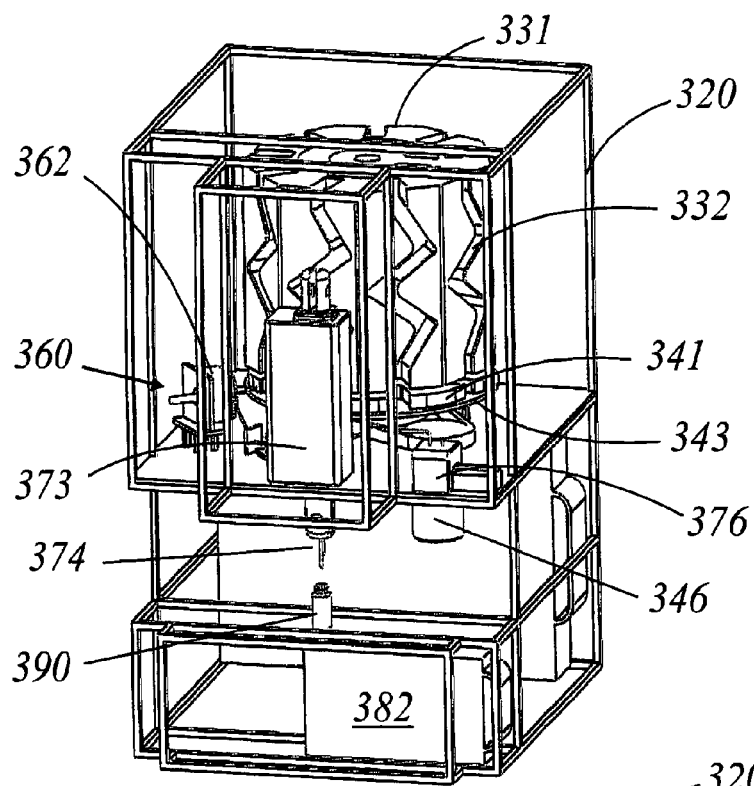
FIGS. 29A and 29B are perspective views of the interior of the embodiment shown in FIG. 28.
Figure 29B:
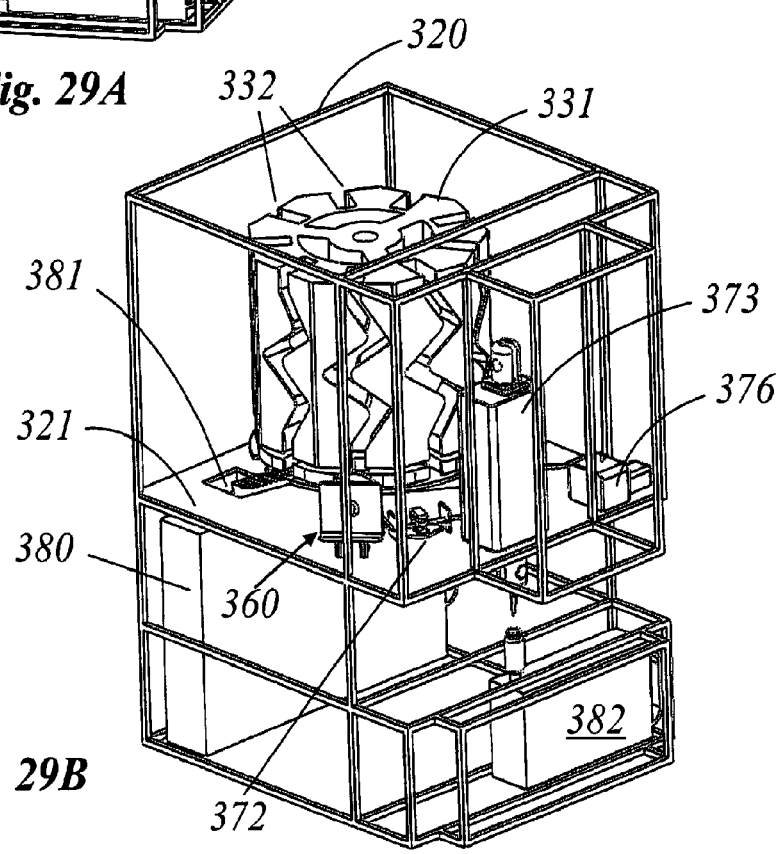
Figure 33A:
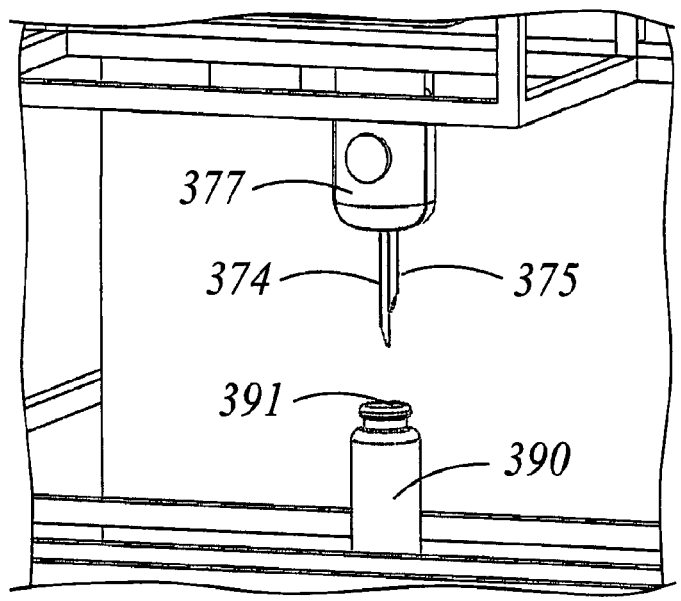
FIGS. 33A and 33B illustrate the transfer of the pharmaceutical agent into the product vial.
Figure 33B:
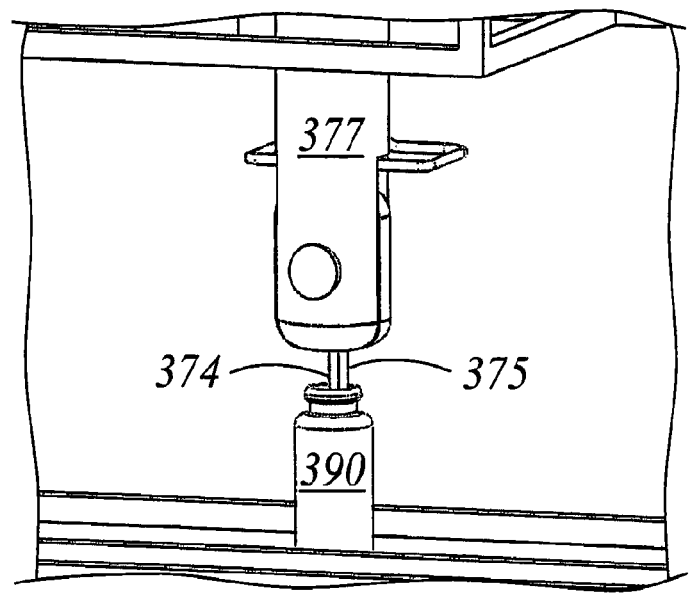

Referring to FIGS. 29A and 29B, system apparatus 300 includes a frame 320 and a platform 321 for supporting the components described below. Referring also now to FIG. 30, in the housing 310 there is positioned the inventory structure 330, which comprises a non-movable carousel body 331 having a plurality of chambers 332 arranged around a circumferential periphery of the carousel body 331 and extending from the top of the carousel body 331 to the bottom. The chambers 332 are each adapted to hold a plurality of pharmaceutical agent-containing capsules 302 in a top to bottom array. The capsules each have a generally cylindrical body portion 303 fabricated from a sturdy puncture resistant plastic, which may be either flexible or rigid. However, the end 304 of the capsule is configured with a resilient film such as rubber adapted to be easily penetrated by a hypodermic needle so as to permit transfer of the pharmaceutical agent from the capsule 302 to a product vial 390 (FIGS. 33A and 33B). The chambers 332 are radially oriented and configured to hold elongated capsules 302 in a lateral orientation such that the ends 304 of the capsules face radially outward. In an embodiment the chambers 232 are zig-zag shaped although they can also be linear, or part linear and part zig-zag.

Figure 31:
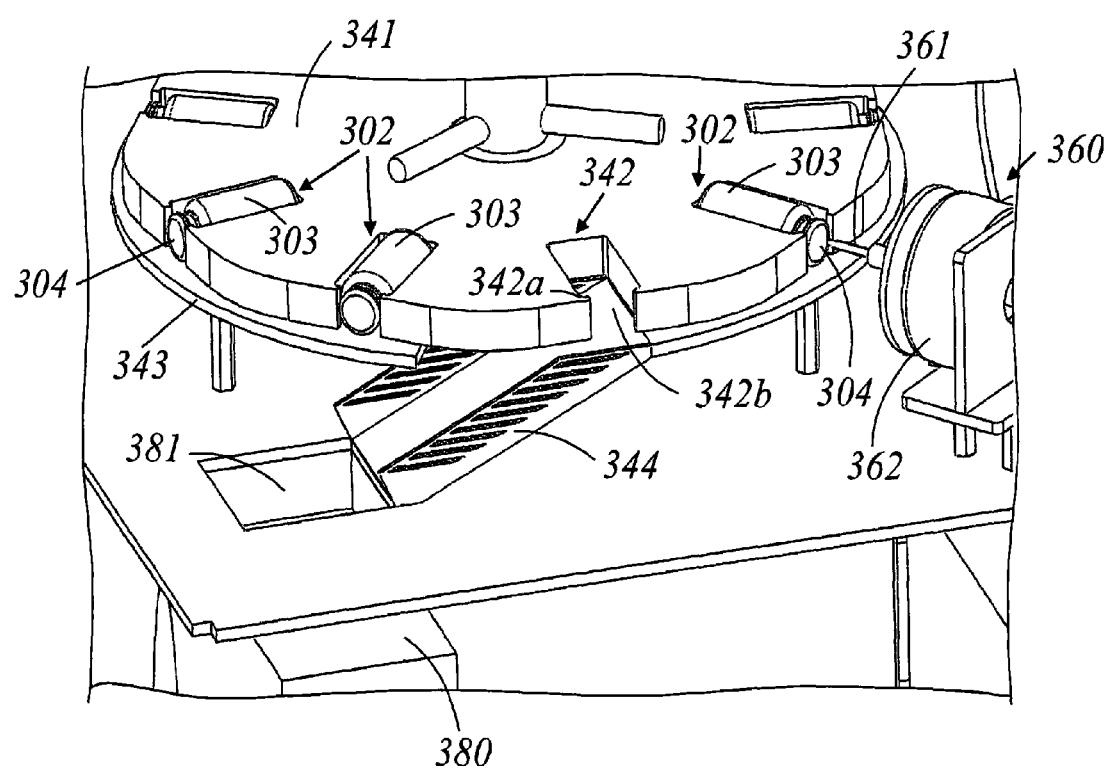
FIG. 31 is a perspective view of the working cylinder and blocking plate as well as the means for puncturing the capsule and disposal of the capsule.
Figure 32A:
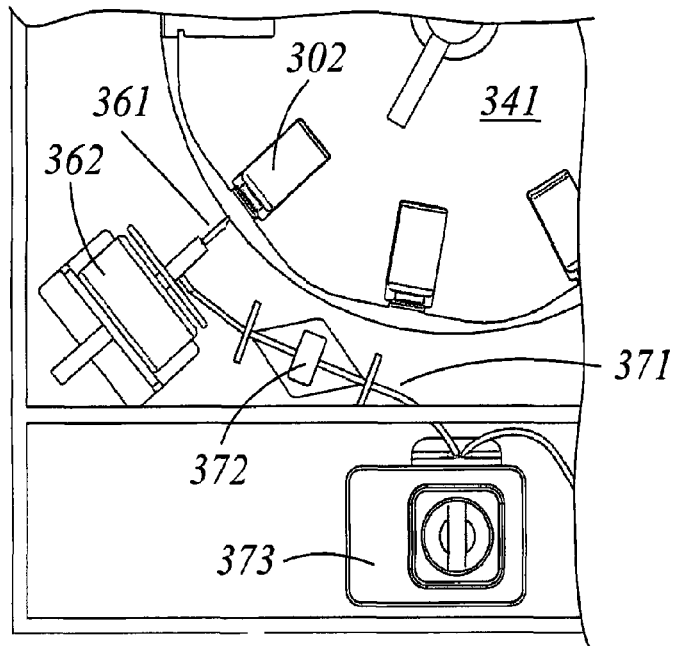
FIGS. 32A and 32B are plan views illustrating the puncturing of the capsule by the extraction needle.
Figure 32B:
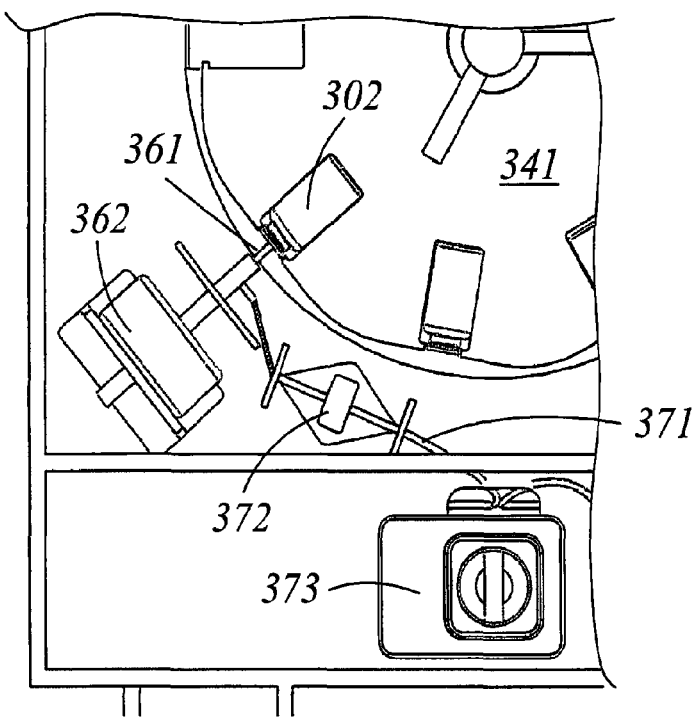

Referring to FIG. 31, beneath the carousel body 331 is a means for selecting a capsule and moving the capsule to a processing area which includes a working cylindrical plate 341 having a plurality of notches 342 disposed around the circumferential periphery of the plate 341, each notch being configured and dimensioned to hold a single capsule 302 in a radial configuration. The notches 342 can be aligned with channels 331 to permit the bottommost capsule 302 in a channel to drop into a corresponding notch 342. Notches 342 preferably have inward directed ridges 342a, which constrict the radial opening 342b of the notch to prevent the capsule 302 from sliding out of opening 342b. The working cylindrical plate 341 is rotatable, and adapted move selected capsules into a processing area as described below. The capsules can roll or slide on the blocking plate 343 below the working cylindrical plate 341 as the working plate 341 rotates.

Beneath the working cylindrical plate 341 is a preferably non-rotatable blocking plate 343, which prevents the capsules 302 in the notches 342 from dropping out of the bottom of notches 342. However, the blocking plate 343 includes a gate 344, which is movable between a closed position and an open position. When gate 344 is in the open position and a notch 342 is aligned with the gate 344, any capsule in the notch is allowed to drop through the gate 344 and into the spent capsule discard bin 380 through opening 381 in platform 321. Accordingly, after the pharmaceutical agent has been drawn out of a capsule 302, the working plate 341 is rotated to move the notch 342 with the spent capsule into alignment with the gate 344, the gate 344 is then opened and the spent capsule is discarded into the spent capsule discard bin 380 for subsequent removal from the system apparatus 300 through door 317 in the housing. A motor 346 positioned beneath platform 321 in the housing portion 310 (FIG. 29A) rotates the working cylindrical plate 341 in response to operating instructions.

Referring also now to FIGS. 31, 32A, 32B, 33A and 33B, the working cylindrical plate is rotated to move a selected capsule 302 to a processing area wherein the capsule is aligned with a means for puncturing the capsule and transferring the pharmaceutical agent from the capsule to the product vial. More specifically, the apparatus 300 includes an extraction needle 361, which is moved by solenoid 362 from a position wherein the extraction needle is spaced apart from the end 304 of the capsule to a position wherein it punctures the end 304 of the capsule. The pharmaceutical agent is drawn out of the capsule by a negative pressure through a fluid line 371. A pinching valve 372 regulates the flow of fluid through the fluid line 371. In order to develop the negative pressure to withdraw the pharmaceutical agent, as shown in FIGS. 33A and 33B, an injection nozzle 374 and vacuum channel 375 mounted to a piston 377 are aligned with a product vial 390 positioned within product vial chamber 322 (FIG. 28) and moved by linear actuator 373 (FIGS. 29A and 29B) from an upper position wherein the injection nozzle 374 and vacuum channel 375 are spaced apart from the product vial 390 to a lower position wherein the injection nozzle 374 and vacuum channel 375 penetrate a rubber seal at the top end 391 of the product vial 390 (FIGS. 33A and 33B). The vacuum channel 375 is preferably shorter than the injection nozzle 374. In an embodiment the injection nozzle can be moved laterally to align the injection nozzle with the product vial. The vacuum channel 375 is connected by a vacuum line to a vacuum pump 376 (FIGS. 32A and 32B), which is actuated to draw a vacuum in the interior of the product vial 390. This vacuum then draws the fluid pharmaceutical agent from the capsule 302 through the fluid line 371 and injection nozzle 374, and into the product vial. A quantity of the transferred solution can be controlled by power of the vacuum pump 376 and transporting time which is regulated by the valve 372. When the contents of one capsule have been transferred it is moved over gate 344 and dropped into the spent capsule discard bin 380. If another capsule is to be used the process is repeated. If no more capsules 302 are to be used the injection nozzle 374 is withdrawn upward and the product vial 390 removed from product vial chamber 322, which uncovers fluid drain 382 in product vial chamber 332.

Figure 34B:
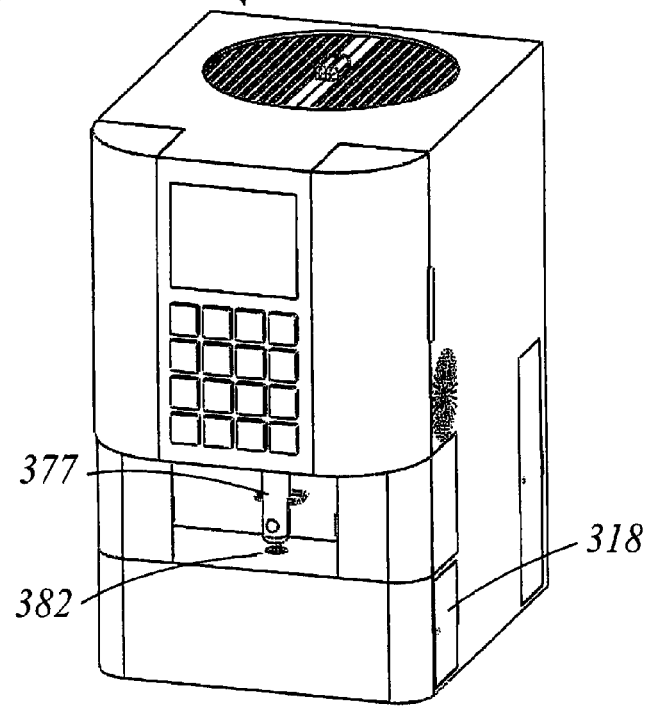

Referring also now to FIGS. 34A and 34B, the system is then flushed with an antiseptic cleaning fluid. The injection nozzle 374 is moved downward such that it at least partially enters fluid drain 382. A capsule 302 containing a cleaning fluid of, for example, ethanol and/or deionized sterile water is punctured as described above and the pressure forces the cleaning fluid through the system whereupon it exits the injection nozzle 374 and passes through the fluid drain 382 having a rubber film which is penetrated by the injection nozzle, and into a spent fluid container (not shown). The accumulation of spent fluid in the container can be removed through door 318 in the housing and discarded. An annular recess around the mouth of the fluid drain 382 can be dimensioned so as to receive the bottom of the product vial and thereby serve as a vial retainer to stabilize the product vial.

In an alternative embodiment of system apparatus 300, all of the pharmaceutical agent-containing capsules can be pressurized. Although such an alternative will be similar to embodiment 300 described above, in this alternative embodiment, the vacuum pump 376 and vacuum channel 375 can be omitted as the withdrawal of the pharmaceutical agent will be accomplished by positive pressure. A quantity of the transferred solution can be controlled by the valve 372 since the pressure inside the capsules is pre-determined and packaged.

Figure 35:
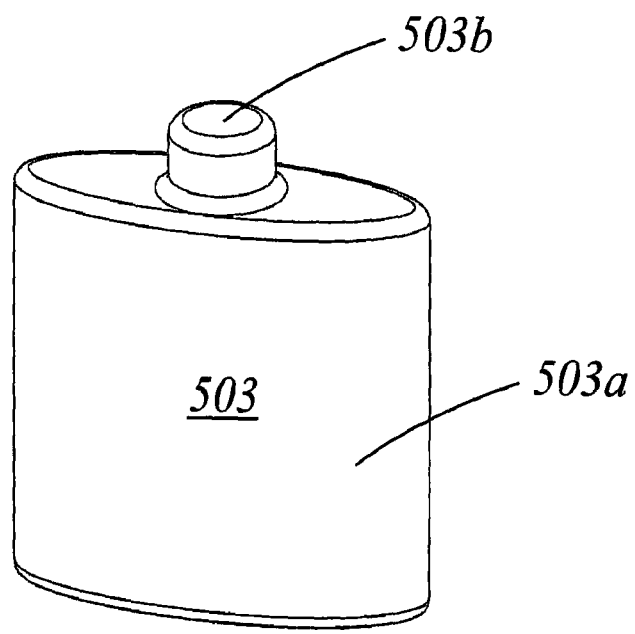
FIG. 35 illustrates an alternative configuration of the pharmaceutical agent-containing capsule.

Referring now to FIG. 35, in an embodiment the capsule as illustrated by capsule 503 can have a rectangular body with an elliptical cross-section 503a and an end 503b of resilient rubber material.

Figure 36:
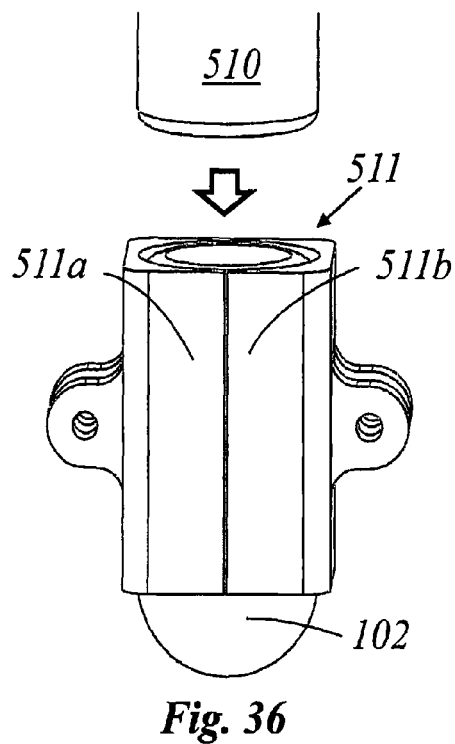
FIG. 36 illustrates the application of positive pressure in a vertical direction to a capsule to expel pharmaceutical agent therefrom.

FIG. 36 illustrates the application of positive pressure in a vertical direction to a capsule 504 to expel pharmaceutical agent therefrom. The capsule 504 is securely held between jaws 511a and 511b of clamping mechanism 511.

Figure 37A:
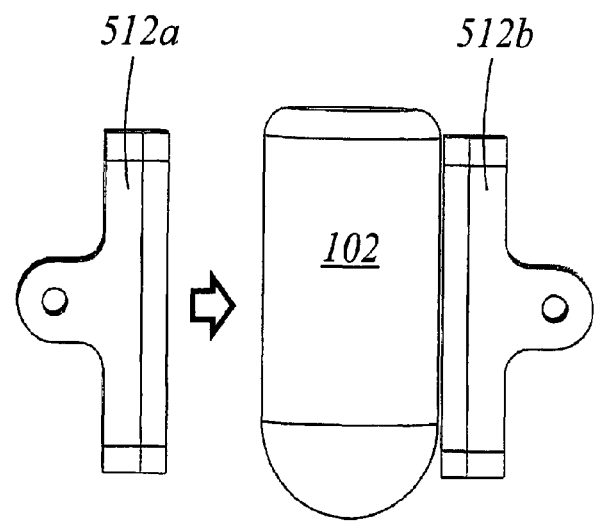
FIGS. 37A and 37B illustrate the application of lateral positive pressure to a capsule to expel pharmaceutical agent therefrom.
Figure 37B:
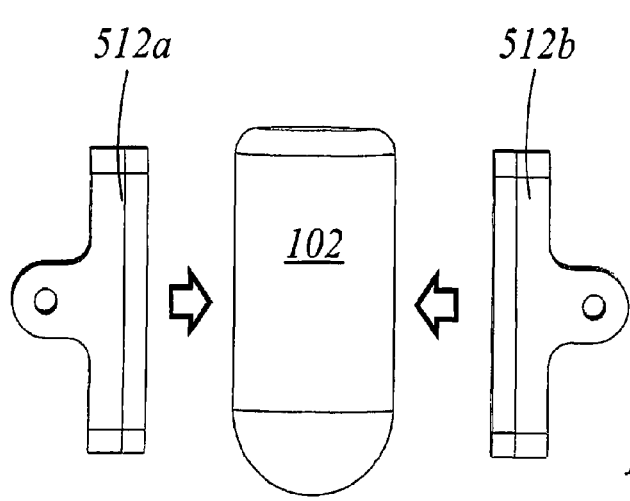

FIGS. 37A and 37B illustrate the application of lateral positive pressure to a capsule to expel pharmaceutical agent therefrom by jaws 512a and 512b of a caliper mechanism. In FIG. 37A jaw 512b is stationary while jaw 511a is moved to apply pressure to the capsule 504. In FIG. 37B both jaws 512a and 512b are moved.

Figure 38:
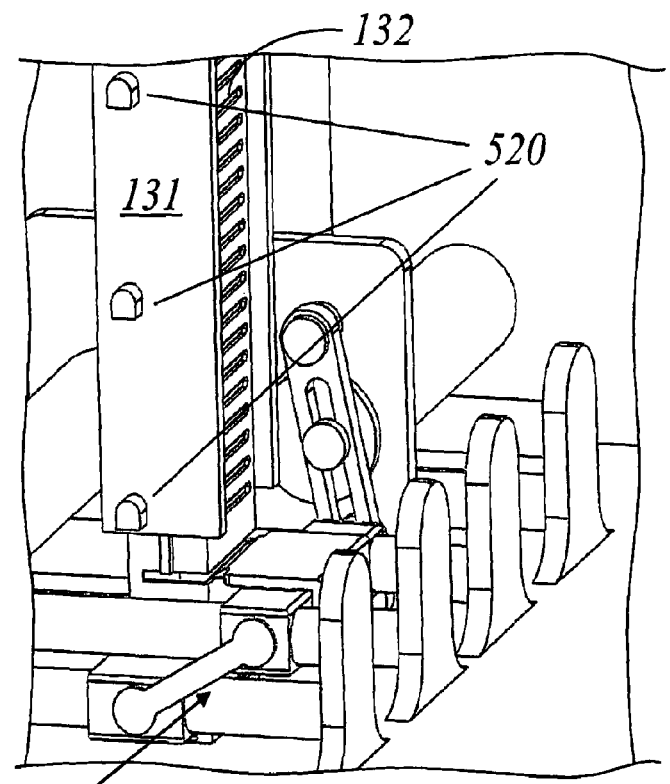
FIGS. 38 to 43D illustrate the placement of sensors in the system apparatus of the invention to monitor the positioning of capsules and various components of the apparatus; and, FIG. 44 illustrates the loading of linear channel members into a carousel shaped inventory structure.

FIG. 38 illustrates the placement of sensors 520 in apparatus 100 to monitor the quantity of capsules loaded into racks 131.

Figure 39:
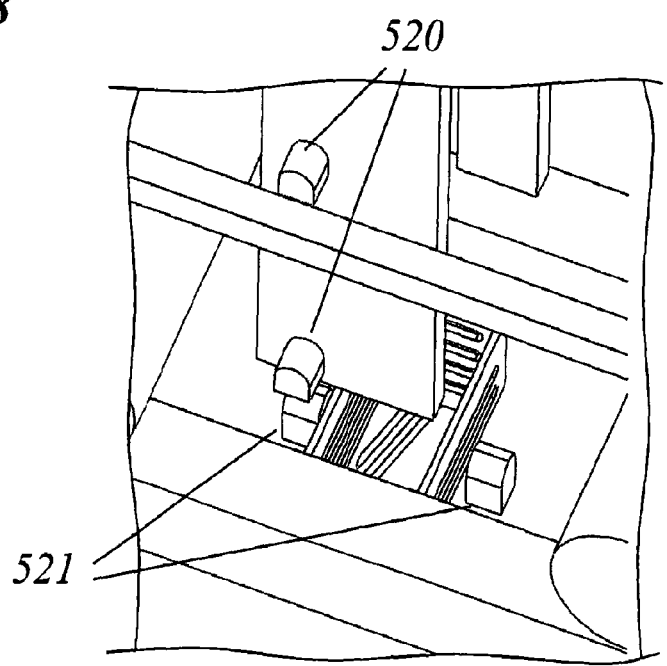

FIG. 39 illustrates the placement of sensors 521 to monitor capsule loading below the racks 131 at the loading slide, gate 141.

Figure 40:
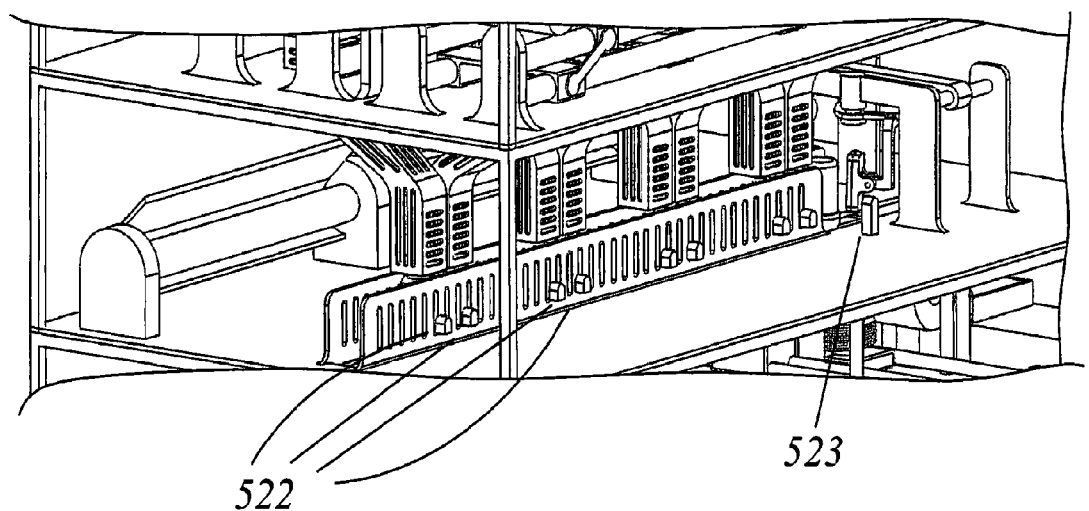

FIG. 40 illustrates the placement of sensors 522 along the guide channel 154 to monitor capsule loading in the conveyor system, belt 151, and also illustrates the placement of sensors 523 at the processing area where the capsules are squeezed and punctured.

Figure 41:
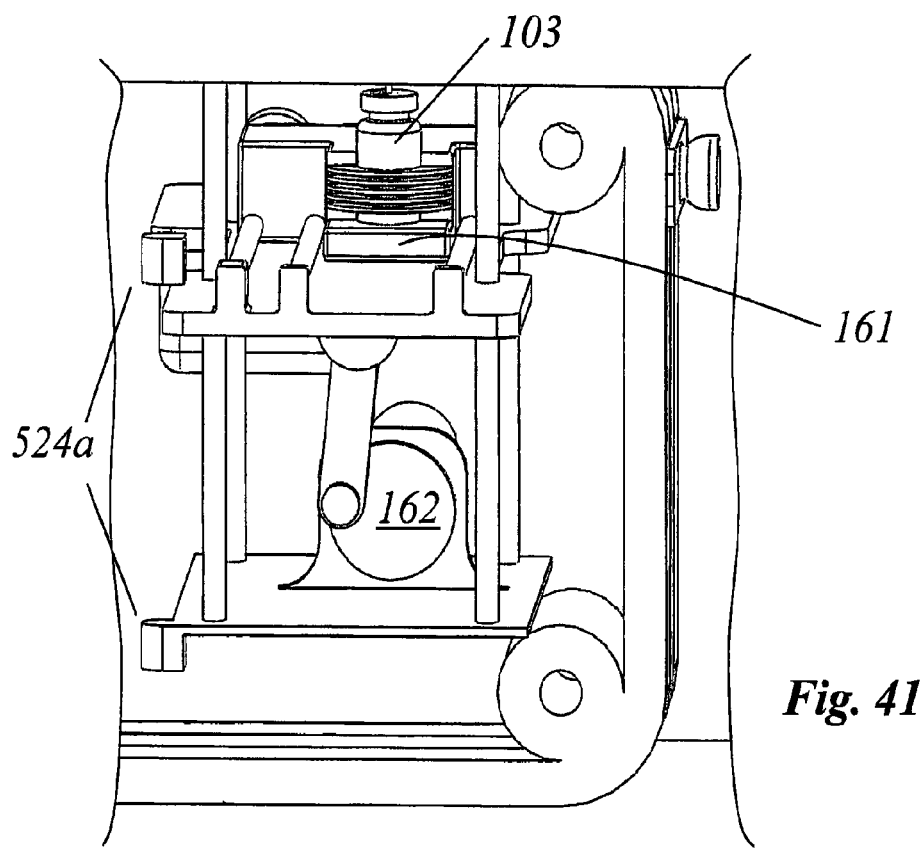

FIG. 41 illustrates the placement of sensors 524a to monitor the lifting of the product vial 103 on the loading platform 161 by crank 162 to puncture the capsule.

Figure 42:
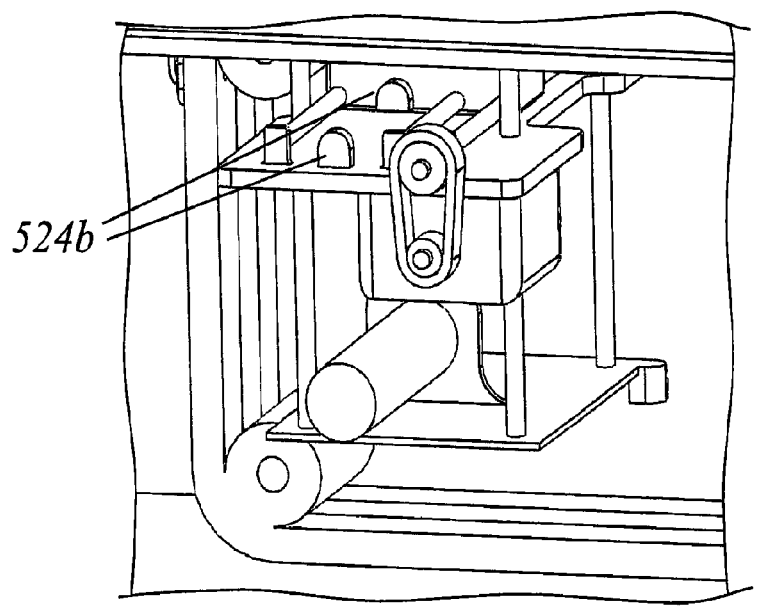
Figure 43A:
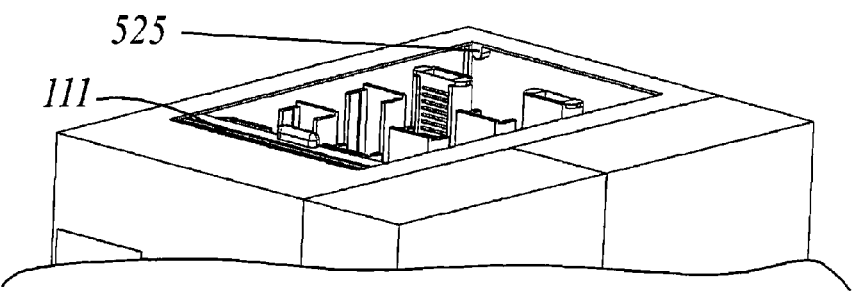
Figure 43B:
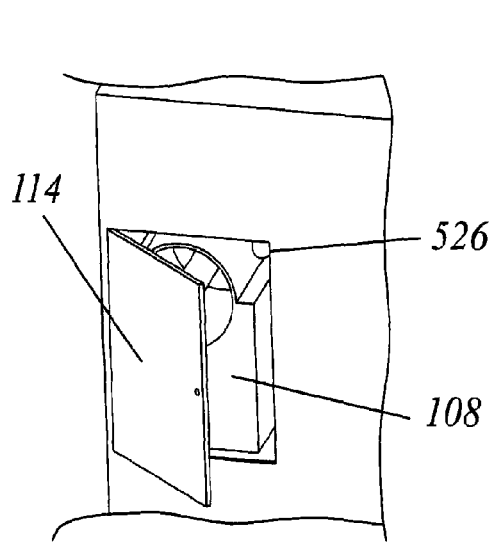
Figure 43C:
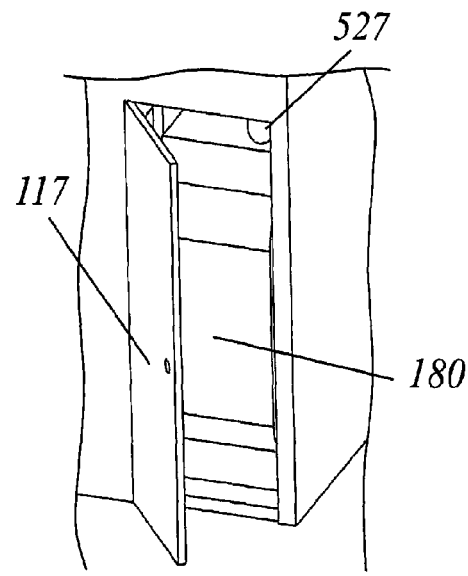
Figure 43D:
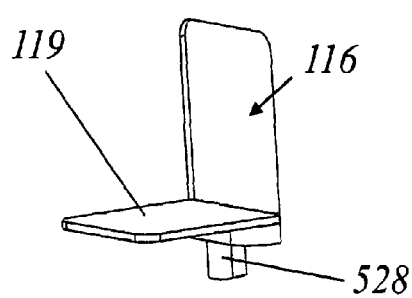

FIG. 42 illustrates the placement of sensors 524b to monitor the lateral movement of the product vial 103 on the loading platform 161;

FIGS. 43A, 43B 43C and 43D illustrate the placement of sensors 525, 526, 527 and 528 at lid 111, printer door 114, capsule disposal door 117 and vial loading door 119, respectively, to monitor the open or closed position of the doors.

Figure 44:
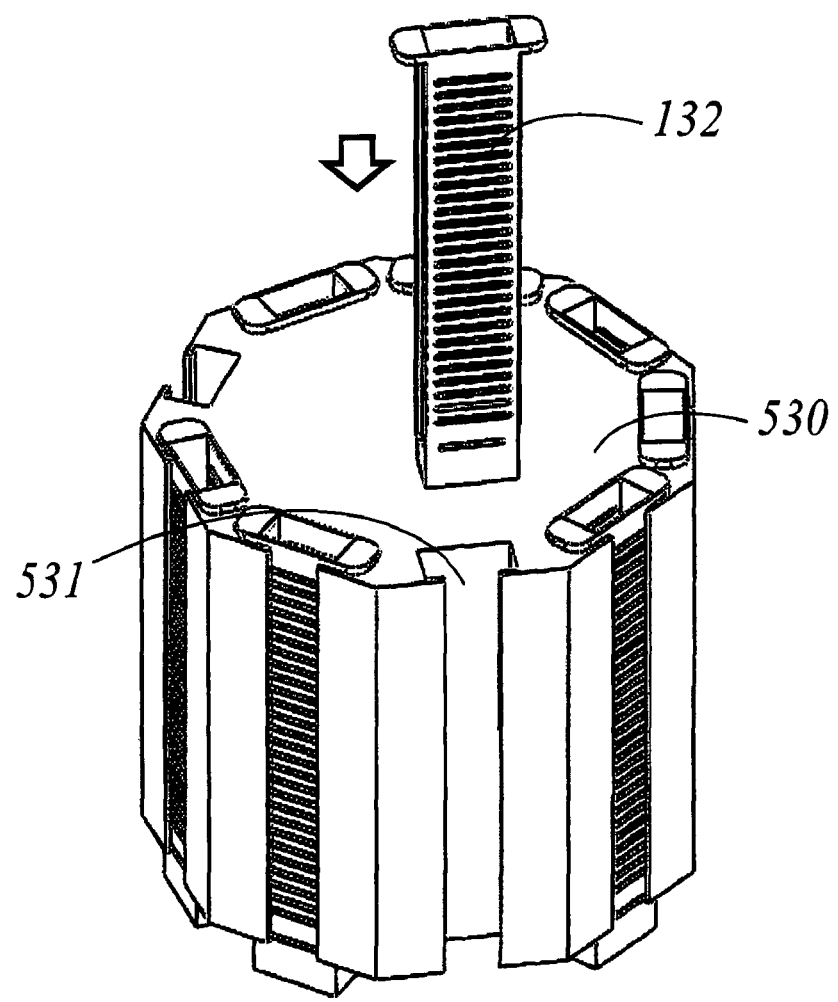

FIG. 44 illustrates the loading of channel members 132 in linear notches 531 of a carousel shaped inventory structure 530 instead of vertical racks 131.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A system for compounding pharmaceutical agents for injection treatment of a patient, which comprises: a) a housing enclosing an interior space; b) an inventory structure having a plurality of chambers for individually holding one or more pharmaceutical agent-containing single use capsules, wherein each capsule has a volume capacity of from about 0.1 to about 10.0 mL liquid; c) means for selecting capsules in accordance with predetermined pharmaceutical agents contained in said capsules; d) means for moving the selected capsules to a processing area; e) means for sequentially transferring a controlled quantity of the predetermined pharmaceutical agent with direct fluid communication from each selected capsule to a product container under positive or negative pressure; and f) means for automatically discarding spent capsules from which the pharmaceutical agents have been removed after a single use, wherein the system is configured to limit the capsules to a single use, and wherein the means for transferring the pharmaceutical agent comprises a means for mechanically compressing the capsule to provide a positive external pressure for moving the pharmaceutical agent from the capsule through a needle and into the product container.

2. The system of claim 1 further including means in the processing area for puncturing the selected capsules.

3. The system of claim 1 wherein the chambers of the inventory structure include a plurality of vertical racks for individually holding a plurality of channels members, each channel member holding a plurality of capsules in a vertical array, and each channel member having a bottom end.

4. The system of claim 3 wherein the means for selecting capsules includes a capsule separation mechanism at the bottom end of each channel, the capsule separation mechanisms being individually movable between a first position wherein the bottom end of the respective channel is closed to prevent passage of a capsule through the bottom end of the channel, and a second position wherein the bottom end of the channel is open to permit passage of a capsule therethrough.

5. The system of claim 1 wherein the means for moving the selected capsules to the processing area comprises a linear transport system.

6. The system of claim 2 wherein the product container is a product vial and the means for puncturing the capsule comprises a cap applied to the product vial, the cap possessing a needle and an air vent; and, a mechanism for piercing the capsule with the needle.

7. The system of claim 1 wherein the means for discarding the spent capsules comprises a waste bin positioned in the interior of the housing into which the spent capsules are dropped.

8. The system of claim 1 wherein the inventory structure comprises a carousel, wherein the chambers are arranged around a circumferential periphery of the carousel, and the capsules are disposed within the chambers or in linear channel members removably insertable in the chambers.

9. The system of claim 8 wherein the chambers have a linear or zig-zag configuration.

10. The system of claim 8 wherein the capsules have an elongated cylindrical or prolate configuration and are horizontally or vertically oriented in respective chambers.

11. The system of claim 2 wherein the means for puncturing the capsules includes an extraction needle movable between a first position and a second position wherein the extraction needle pierces the end of a selected capsule sufficiently to draw pharmaceutical agent therefrom.

12. The system of claim 8 including an injection system positioned within the housing, the injection system including an injection nozzle which is movable between an initial upper position and a lower position for insertion into the product container.

13. The system of claim 12 wherein the injection nozzle is also laterally movable.

14. The, system of claim 12 further including a vacuum conduit associated with the injection nozzle.

15. The system of claim 12, further comprising a means for disposing waste produced by the cleaning of the injection system, wherein the means for disposing waste produced by the cleaning of the injection system comprises a drain leading to a waste solution container within the interior of the housing.

16. The system of claim 15, further comprising a means for cleaning the injection system, wherein the means for cleaning the injection system includes a capsule containing a sterile cleaning solution comprising ethanol and/or deionized water.

17. The system of claims 14 further including a vacuum pump.

18. The system of claim 1 wherein the product container is a hypodermic syringe having a needle attached to one end, a plunger, and a removable cap covering the needle, and wherein the means for transferring the pharmaceutical agent comprises mounting means for holding the hypodermic syringe, said mounting means being movable between a first position wherein the hypodermic syringe is spaced apart from the selected capsule to a second position wherein the needle penetrates the capsule, wherein the mounting means further includes means for grasping and pulling the plunger of the hypodermic syringe, and wherein the system further includes means for removing the cap.

19. The system of claim 1 further including a UV sterilizing lamp positioned in the interior of the housing.

20. The system of claim 1 wherein, the pharmaceutical agents include pharmaceutically effective amounts of one or more of vitamins, growth hormone, glucosamine, omega-3 fatty acids, onabotulinumtoxin A and/or insulin.

21. The system of claim 1 wherein the capsules and chambers are color coordinated.

22. The system of claim 1 further including a plurality of sensors positioned in the interior of the housing for monitoring the capsule inventory and operation of the system.

23. The system of claim 1 further including a label printer.

24. The system of claim 1 wherein the capsules are pressurized.

25. The system of claim 1 further including information input and output units.

26. The system of claim 1 wherein the pharmaceutical agents are injectables comprising one or more of vitamins, growth hormone, glucosamine, omega-3 fatty acids, onabotulinumtoxin A, and/or insulin, and the patient is a human or animal.

27. A method for compounding pharmaceutical agents for injection treatment of a patient, comprising: a) storing a plurality of pharmaceutical agent-containing capsules in an inventory structure; b) selecting one or more capsules according to the pharmaceutical agents contained therein; c) puncturing the selected capsules with an extraction device; d) withdrawing a quantity of pharmaceutical agents from the selected capsules under positive or negative pressure and transferring the withdrawn pharmaceutical agents to a product container; e) discarding spent capsules from which the pharmaceutical agents have been withdrawn after a single use of the capsules, wherein the method requires that the capsules be limited to a single use, and wherein the transferring the withdrawn pharmaceutical agents to a product container comprises using a means for mechanically, compressing the capsule to provide a positive external pressure for moving the pharmaceutical agent from the capsule through a needle and into the product container.

* * * * *